(12) United States Patent
Young

(10) Patent No.: US 6,500,405 B1
(45) Date of Patent: Dec. 31, 2002

(54) USE OF CERTAIN AMIDES AS PROBES FOR DETECTION OF ANTITUBULIN ACTIVITY AND RESISTANCE MONITORING

(75) Inventor: David Hamilton Young, Ambler, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/433,463

(22) Filed: Nov. 4, 1999

Related U.S. Application Data

(63) Continuation-in-part of application No. 08/964,799, filed on Nov. 5, 1997, now abandoned.
(60) Provisional application No. 60/030,920, filed on Nov. 14, 1996.

(51) Int. Cl.[7] .............................................. A61K 49/00
(52) U.S. Cl. .......................... 424/9.2; 435/7.1; 562/400
(58) Field of Search ...................... 435/7.1, 4; 424/9.2; 514/359, 417, 479, 538, 617

(56) References Cited

U.S. PATENT DOCUMENTS

| | | | |
|---|---|---|---|
| 3,661,991 A | 5/1972 | McNulty et al. | |
| 4,568,649 A | 2/1986 | Bertoglio-Matte | |
| 4,863,940 A | 9/1989 | Sharma | |
| 5,254,584 A | 10/1993 | Michelotti et al. | |
| 6,140,362 A * | 10/2000 | Michelotti et al. | 514/514 |

FOREIGN PATENT DOCUMENTS

EP 843018 A1 * 5/1998

OTHER PUBLICATIONS

Hamel, E., *Medicinal Research Reviews*, vol. 16, No. 2, 207–231, 1996.
Duanmu, C. et al., *Cancer Research*, 49, 1344–1348, 1989.
Zweig, M. H. and Chignell, C. F., *Biochemical Pharmacology*, vol. 22, 2141–2150, 1973.
Bai, R. et al., *Journal of Biological Chemistry*, vol. 265, 17141–17149, 1990.
Davidse, L. C. and Ishii, H., *Modern Selective Fungicides*, ed. by H. Lyr, 305–322, 1995.
Koenraadt, H. et al., *Phytopathology*, 82, 1348–1354, 1992.
Yarden, O. and Katan, T., *Phytopathology*, 83, 1478–1483, 1993.
Thrower, D. et al., *Methods in Cell Biology*, vol. 37, 129–145, 1993.

* cited by examiner

Primary Examiner—Dameron L. Jones
(74) Attorney, Agent, or Firm—Clark B. Carpenter; Kenneth B. Ludwig

(57) ABSTRACT

This invention relates to methods for screening compounds for antitubulin activity, evaluation of cells for sensitivity to antitubulin drugs, resistance monitoring and quantifying tubulin using certain amides that inhibit the growth of eukaryotic cells as probes in binding assays, said amides having the structural formula

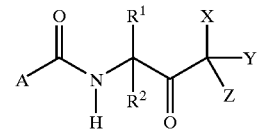

wherein
A is cycloalkyl, alkyl, haloalkyl, alkylthio, haloalkylthio, alkenyl, haloalkenyl, alkynyl, haloalkynyl, alkoxy, haloalkoxy, or phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl or benzyl, all optionally substituted in an acceptable manner with up to 4 substituents;
$R^1$ and $R^2$ are each independently a hydrogen atom, alkyl, haloalkyl, alkenyl, haloalkenyl, alkynyl or haloalkynyl, provided that both $R^1$ and $R^2$ are not a hydrogen atom; and
X, Y and Z are each independently a hydrogen atom, halo, cyano, thiocyano, isothiocyano or alkylsulfonyloxy, provided that at least one of X, Y and Z is not a hydrogen atom; or
the optical enantiomers thereof.

15 Claims, 3 Drawing Sheets

USE OF CERTAIN AMIDES AS PROBES FOR DETECTION OF ANTITUBULIN ACTIVITY AND RESISTANCE MONITORING

RELATED APPLICATIONS

This application is a continuation-in-part to application Ser. No. 08/964,799 filed Nov. 5, 1997 now abandoned, which claims priority to Provisional Application Ser. No. 60/030,920 filed Nov. 14, 996, now abandoned.

BACKGROUND OF THE INVENTION

Microtubules are intracellular filamentous structures present in all eukaryotic cells. As components of different organelles such as mitotic spindles, centrioles, basal bodies, cilia, flagella, axopodia and the cytoskeleton, microtubules are involved in many cellular functions including chromosome movement during mitosis, cell motility, organelle transport, cytokinesis, cell plate formation, maintenance of cell shape and orientation of cell microfibril deposition in developing plant cell walls. The major component of microtubules is tubulin, a protein composed of two subunits called alpha and beta. An important property of tubulin in cells is the ability to undergo polymerization to form microtubules or to depolymerize under appropriate conditions. This process can also occur in vitro using isolated tubulin.

Microtubules play a critical role in cell division as components of the mitotic spindle, an organelle which is involved in distributing chromosomes within the dividing cell precisely between the two daughter nuclei. Various drugs and pesticides prevent cell division by binding to tubulin or to microtubules. Anticancer drugs acting by this mechanism include the alkaloids vincristine and vinblastine, and the taxane-based compounds paclitaxel and docetaxel {see, for example, E. K. Rowinsky and R. C. Donehower, *Pharmacology and Therapeutics*, 52, 35–84 (1991)}. Other antitubulin compounds active against mammalian cells include benzimidazoles such as nocodazole and natural products such as colchicine, podophyllotoxin and the combretastatins. Benzimidazole compounds which bind to tubulin are also widely used anthelmintics {McKellar, Q. A. and Scott, E. W., *J. Vet. Pharmacol. Ther.*, 13, 223–247 (1990)}. Anti-tubulin herbicides are described in "The Biochemical Mode of Action of Pesticides", by J. R. Corbett, K. Wright and A. C. Baillie, pp. 202–223, and include dinitroanilines such as trifluralin, N-phenylcarbamates such as chlorpropham, amiprophos-methyl, and pronamide. Fungicides believed to act by binding to tubulin include zarilamide {Young, D. H. and Reitz, E. M., *Proceedings of the 10th International Symposium on Systemic Fungicides and Antifungal Compounds*, Reinhardsbrunn, ed by H. Lyr and C. Polter, 381–385, (1993)}, the benzimidazoles benomyl and carbendazim, and the N-phenylcarbamate diethofencarb {Davidse, L. C and Ishi, H. in "Modern Selective Fungicides", ed. by H. Lyr, 305–322 (1995)}.

Due to the success of tubulin as a biochemical target for drugs and pesticides, there is considerable interest in discovering new compounds which bind to tubulin. Various cell-free methods are available for detecting such compounds. A common method involves measuring the ability of test compounds to inhibit the polymerization of isolated tubulin into microtubules in vitro {see for example, E. Hamel, *Medicinal Research Reviews*, 16, 207–231 (1996)}. In a second method, interactions of test compounds with isolated tubulin can be detected in binding assays by measuring the ability of the test compound to influence binding of a second tubulin-binding ligand, used as a probe. (The term "test compound" means a compound which one wishes to evaluate, i.e. to test, for its ability to affect tubulin). Typically, the probe is radiolabeled to enable binding to be measured. A test compound which binds to tubulin may influence binding of the probe by binding to the same site on the tubulin protein as the probe, and thus reduce the amount of probe which binds. Alternatively, binding may be influenced by means of an "allosteric" interaction in which the test compound binds to a different site from that of the probe and induces a conformational change in the tubulin protein which affects the binding site of the probe. Such an allosteric interaction may either increase or decrease binding of the probe. A third approach involves measuring the effect of test compounds on tubulin-associated guanosine triphosphatase activity {Duanmu, C., Shahrik, L. K., Ho, H. H. and Hamel, E., *Cancer Research*, 49, 1344–1348 (1989)}.

To screen large numbers of compounds by any of these methods is feasible at present only using tubulin from mammalian brain tissue, since it has not been possible to isolate sufficiently large amounts of purified tubulin from other sources. This limits the usefulness of these methods since many anti-tubulin compounds show great specificity with respect to their effects on microtubules from different sources. For example, the herbicides oryzalin and amiprophosmethyl inhibit the polymerization of plant tubulin but not brain tubulin, whereas colchicine is more than 100-fold more effective as an inhibitor of brain tubulin polymerization than of plant tubulin polymerization {Morejohn, L. C. and Fosket, D. E., 'Tubulin from Plants, Fungi, and Protists', in "Cell and Molecular Biology of the Cytoskeleton", ed. by J. W. Shay, 257–329 (1986)}.

The present invention relates to the use of certain amide derivatives, known to inhibit the growth of eukaryotic cells, including fungal and plant cells {see, for example, U.S. Pat. Nos. 3,661,991, 4,863,940 and 5,254,584}. Said amides have now been found useful as probes in binding assays to screen compounds for antitubulin activity, a use which U.S. Pat. Nos. 3,661,991, 4,863,940 and 5,254,584 neither disclose nor suggest. While radiolabeled probes such as colchicine {see for example, M. H. Zweig and C. F. Chignell, *Biochemical Pharmacology*, 22, 2141–2150 (1973)} and vinblastine (see for example, R. Bai et al., *Journal of Biological Chemistry*, 265, 17141 (1990)} have been used extensively in binding assays using isolated tubulin, these compounds bind noncovalently to tubulin.

One advantage of the amide derivatives of this invention over existing antitubulin compounds in competitive binding assays results from their unique ability to bind covalently in a highly specific manner to tubulin, specifically to the beta-subunit of tubulin. (A covalent bond is a nonionic chemical bond characterized by the sharing of electrons by two atoms). In binding assays it is necessary to measure the amount of the probe which is bound to tubulin, and this generally involves separating the tubulin-bound probe from unbound probe. In the case of the amides, since binding is covalent, the tubulin-bound probe is chemically stable allowing easy separation from the unbound probe by methods such as filtration or centrifugation. This enables their use not only in assays using isolated tubulin but also in assays using whole cells, crude cell extracts, and partially purified tubulin preparations, thus obviating the need for isolated tubulin and enabling tubulin-binding assays to be carried out in many different types of cell or cell extract.

One aspect of the present invention involves use of amide probes in binding assays to screen large numbers of compounds in order to identify those compounds with antitubulin activity using whole cells, cell extracts or isolated tubulin. For example, test compounds which bind to plant or fungal tubulin may be detected in assays using plant or fungal cells, thus providing a means of detecting antitubulin compounds with herbicidal or fungicidal activity. Similarly, amide probes may be used to detect compounds which bind to tubulin in mammalian cells or cell extracts, thus providing a means of detecting antitubulin compounds with anticancer activity.

A second aspect of the current invention involves use of amide probes in binding assays to evaluate the sensitivity of a cell population to an antitubulin compound. For example, the current invention can be used to evaluate the sensitivity of a tumor cell population to an antitubulin drug such as paclitaxel, vincristine or vinblastine, thus providing a means of predicting drug sensitivity of a patient's tumor at the time of diagnosis or relapse using cells isolated by biopsy, and consequently guiding selection of the optimal chemotherapy regimen. Frequently, treatment of neoplasms with a particular antitubulin drug results in resistance development due to a reduced accumulation of drug in the cell. The current invention also provides a method for determining sensitivity of such resistant cells to antitubulin drugs. Various types of in vitro drug sensitivity tests have been used to select drugs more likely to be effective against tumor cells of a particular patient prior to their in vivo application {Cortazar, P. et al., Clinical Cancer Research, 3, 741–747 (1997), Arps, H. et al., Int. J. Immunotherapy, III, 229–235 (1987)}. Such assays typically involve cell culture of the isolated tumor cells or xenotransplantation using transplant-bearing mice, and require several days to multiple weeks to obtain results. In the current invention, the sensitivity of isolated tumor cells to antitubulin drugs can be determined by measuring the ability of said antitubulin drugs to influence binding of an amide probe to the cells, cell extracts or isolated tubulin. Since this method does not require culture of the isolated cells, it can provide sensitivity data within a few hours allowing drug sensitivity to be determined more rapidly.

A third aspect of the present invention involves another approach to the use of amide probes in binding assays to evaluate sensitivity of eukaryotic cells to pesticides or drugs which act by binding to tubulin. Specifically, this approach is useful in resistance monitoring for antitubulin pesticides or drugs to detect cells which show altered sensitivity to said antitubulin pesticides or drugs due to modifications in tubulin. Resistance to antitubulin compounds due to modifications in tubulin have occurred in fungal pathogens {Davidse, L. C. and Ishi, H. in "Modern Selective Fungicides", ed. by H. Lyr, 305–322 (1995)}, algae {James, S. W. et al., *Journal of Cell Science*, 106, 209–218 (1993)} and helminths {Beech, R. N. et al., Genetics, 138, 103–110 (1994)}. Resistant cells containing modified tubulin may show a difference in binding affinity for amides, allowing amide probes to be used in binding assays to detect such mutants. Such an assay can be carried out by comparing the rate of binding of an amide probe to cells or extracts of cells previously exposed to the antitubulin pesticide or drug with the rate of binding to untreated control cells or cell extracts.

For example, benzimidazole and thiophanate fungicides such as benomyl (methyl 1-(butylcarbamoyl)benzimidazol-2-ylcarbamate), fuberidazole (2-(2'-furyl)benzimidazole), thiabendazole (2-(4-thiazolyl)benzimidazole), carbendazim (methyl benzimidazol-2-ylcarbamate), thiophanate-methyl (1,2-bis(3-methoxycarbonyl-2-thioureido)benzene, and thiophanate (1,2-bis(3-ethoxycarbonyl-2-thioureido) benzene are known in the art for use against plant pathogenic fungi. However, the use of benzimidazole and thiophanate fungicides over a period of time can result in the development of fungal strains having reduced sensitivity to these fungicides, whereby the fungicides are much less effective in controlling a particular fungal disease. Such "resistant" fungi when isolated as pure cultures typically are from 10-fold to >1,000-fold less sensitive to benzimidazoles and thiophanates than fungi from locations which have not been exposed to these fungicides. Moreover, fungi which develop reduced sensitivity to one benzimidazole or thiophanate fungicide frequently also show reduced sensitivity to other benzimidazole or thiophanate fungicides. The N-phenylcarbamate fungicide diethofencarb is used commercially to control benzimidazole-resistant fungi such as *Botrytis cinerea*. However, its use has led to the development of fungal strains resistant to both benzimidazoles and diethofencarb. Current methods to detect fungal strains resistant to benzimidazoles, thiophanates or diethofencarb are labor-intensive and time-consuming. Some methods involve isolation of pure test cultures followed by in vitro assays of mycelial growth using fungicide-amended agar plates, or in vivo assays involving fungicide-treated leaves. Alternatively, slide germination tests of spores may be carried out in the presence of fungicide. Fungal strains which are resistant to diethofencarb and/or benzimidazoles and thiophanates typically contain modified tubulin proteins {see for example, Koenraadt, H. et al., *Phytopathology*, 82, 1348–1354 (1992) and Yarden, O. and Katan, T., *Phytopathology*, 83, 1478–1483 (1993)}. Benzimidazole-resistant, diethofencarb-sensitive fungal strains typically show enhanced sensitivity to amide derivatives of the present invention, whereas benzimidazole-resistant, diethofencarb-resistant fungal strains typically show reduced sensitivity. While not wishing to be bound by theory, it is believed that amide probes can be used in binding assays to differentiate benzimidazole-resistant, diethofencarb-sensitive fungal strains which show enhanced ability to bind amide probes in assays using whole cells or cell extracts, or benzimidazole-resistant, diethofencarb-resistant fungal strains which show reduced ability to bind amide probes, from strains which are not resistant. Such assays may be less labor-intensive and time-consuming, and may also provide information as to whether the resistance mechanism involves a change in tubulin. Information about the mechanism of resistance may be useful in designing a resistance management strategy.

A fourth aspect of the present invention involves the use of amide probes in binding assays to detect and quantitate tubulin in cells or cell extracts. Tubulin is the subject of intense research due to its success as a target for drugs and pesticides and its important cellular functions. In such studies it is often desirable to detect and quantitate tubulin in cells or cell extracts. At present this is accomplished by various immunoassays {D. Thrower et al., Methods in Cell Biology, vol. 37, pp. 129–145 (1993)}, sodium dodecyl sulfate polyacrylamide gel electrophoresis {B. M. Spiegelman et al., Cell, vol. 12, pp. 587–600 (1977)}, binding to DEAE-cellulose {J. C. Bulinski et al., Analytical Biochemistry, vol. 104, 432–439 (1980)}, or by measuring colchicine-binding activity {Wilson, L., Biochemistry, vol. 9, pp. 4999–5007 (1970)}. Amide probes offer an alternative method to detect and quantitate tubulin based on measurement of amide-binding activity. Use of amide probes obviates the need for antibodies against tubulin, provides a simpler and more rapid method than either sodium dodecyl sulfate polyacrylamide gel electrophoresis or binding to DEAE-cellulose, and is applicable to measurement of tubulin levels in a variety of cells such as plant or fungal cells which are not sensitive to colchicine.

Various methods known to those with skill in the art can be used to detect the binding of amide probes to tubulin in assays using whole cells, crude cell extracts, partially purified tubulin preparations or isolated tubulin. This may, for example, involve the use of radiolabeled or fluorescent amide probes. Typically, the probe is incubated with cells, cell extracts or tubulin preparations and the amount of bound probe is determined following its separation from unbound probe by various separation techniques or a combination of such techniques. Separation techniques include, but are not limited to, centrifugation, chromatography, phase separation, precipitation of either the bound or unbound probe, or adhesion of either the bound or unbound probe to a solid substrate. Scintillation proximity assay technology (U.S. Pat. No. 4,568,649) provides another potential method to measure binding of the probe to tubulin. Yet another method involves detection of amide-bound tubulin, or amide-bound peptides released from tubulin by chemical or enzymatic treatment, by mass spectroscopy techniques.

SUMMARY OF THE INVENTION

One embodiment of this invention is a method for carrying out binding assays, which are useful for screening test compounds for antitubulin activity, comprising (i) incubating eukaryotic cells, cell extracts or isolated tubulin with the said test compound, (ii) adding an amide probe to the eukaryotic cells, cell extracts or isolated tubulin either simultaneously with the addition of the said test compound or subsequent to the addition of the said test compound and measuring the rate of binding of the said amide probe to tubulin in the eukaryotic cell, cell extract or isolated tubulin sample, and (iii) determining the antitubulin activity of the said test compound as indicated by a reduction or enhancement of the rate of binding of the said amide probe to tubulin in the sample containing the said test compound relative to the rate of binding of the said amide probe to tubulin in a control sample lacking the said test compound; said method using the said amide that binds covalently to tubulin and that inhibits the growth of eukaryotic cells, said amide having the structural formula

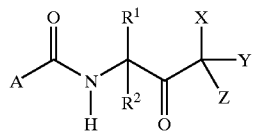

(I)

wherein

A is phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl; or phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl substituted with up to three substituents each independently selected from halo, cyano, $(C_1-C_4)$alkyl, halo$(C_1-C_4)$alkyl, $(C_2-C_4)$alkenyl, halo$(C_2-C_4)$alkenyl, $(C_2-C_4)$alkynyl, halo$(C_2-C_4)$alkynyl, $(C_1-C_4)$alkoxy, halo$(C_1-C_4)$alkoxy, $(C_1-C_4)$alkylthio, halo$(C_1-C_4)$alkylthio, nitro, $-NR^6R^7$, $-CR^8=NOR^9$, $-NHCOOR^{10}$, $-CONR^{11}R^{12}$, and $-COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, $(C_1-C_4)$alkyl, halo$(C_1-C_4)$alkyl, $(C_2-C_4)$alkenyl, halo$(C_2-C_4)$alkenyl, $(C_2-C_4)$alkynyl or halo$(C_2-C_4)$alkynyl, provided that both $R^1$ and $R^2$ are not a hydrogen atom;

$R^6$ and $R^7$ are each independently a hydrogen atom, $(C_1-C_4)$alkyl or $(C_1-C_4)$alkylcarbonyl;

$R^8$ is a hydrogen atom, $(C_1-C_4)$alkyl, $(C_2-C_4)$alkenyl or $(C_2-C_4)$alkynyl;

$R^9$ is a hydrogen atom, $(C_1-C_4)$alkyl, $(C_2-C_4)$alkenyl, $(C_2-C_4)$alkynyl or $(C_1-C_4)$alkylcarbonyl;

$R^{10}$, $R^{11}$, $R^{12}$ and $R^{13}$ are each independently a hydrogen atom, $(C_1-C_4)$alkyl, $(C_2-C_4)$alkenyl or $(C_2-C_4)$alkynyl; and X, Y and Z are each independently a hydrogen atom, halo, cyano, thiocyano or isothiocyano, provided that at least one of X, Y and Z is not a hydrogen atom; or the optical enantiomers thereof.

A second embodiment of this invention is a method for evaluating the sensitivity of a test cell population to an antitubulin compound comprising (i) incubating cells, cell extracts or isolated tubulin of the said test cell population with the said antitubulin compound, (ii) adding an amide probe to the cells, cell extracts or isolated tubulin of the said test cell population either simultaneously with the addition of the said antitubulin compound or subsequent to the addition of the said antitubulin compound and measuring the rate of binding of the said amide probe to tubulin in the cells, cell extracts or isolated tubulin of the said test cell population, and (iii) determining the sensitivity of the said test cell population to the said antitubulin compound by comparing the ability of the said antitubulin compound to affect binding of the said amide probe in the cells, cell extracts or isolated tubulin of the said test cell population with its ability to affect binding of the said amide probe in cells, cell extracts or isolated tubulin from cell populations of known sensitivity to the said antitubulin compound, said method using the said amide that binds covalently to tubulin and that inhibits the growth of eukaryotic cells, said amide having the structural formula

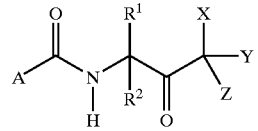

(I)

wherein

A is phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl; or phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl substituted with up to three substituents each independently selected from halo, cyano, $(C_1-C_4)$alkyl, halo$(C_1-C_4)$alkyl, $(C_2-C_4)$alkenyl, halo$(C_2-C_4)$alkenyl, $(C_2-C_4)$alkynyl, halo$(C_2-C_4)$alkynyl, $(C_1-C_4)$alkoxy, halo$(C_1-C_4)$alkoxy, $(C_1-C_4)$alkylthio, halo$(C_1-C_4)$alkylthio, nitro, —$NR^6R^7$, —$CR^8$=$NOR^9$, —$NHCOOR^{10}$, —$CONR^{11}R^{12}$, and —$COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, $(C_1-C_4)$alkyl, halo$(C_1-C_4)$alkyl, $(C_2-C_4)$alkenyl, halo$(C_2-C_4)$alkenyl, $(C_2-C_4)$alkynyl or halo$(C_2-C_4)$alkynyl, provided that both $R^1$ and $R^2$ are not a hydrogen atom;

$R^6$ and $R^7$ are each independently a hydrogen atom, $(C_1-C_4)$alkyl or $(C_1-C_4)$alkylcarbonyl;

$R^8$ is a hydrogen atom, $(C_1-C_4)$alkyl, $(C_2-C_4)$alkenyl or $(C_2-C_4)$alkynyl;

$R^9$ is a hydrogen atom, $(C_1-C_4)$alkyl, $(C_2-C_4)$alkenyl, $(C_2-C_4)$alkynyl or $(C_1-C_4)$alkylcarbonyl;

$R^{10}$, $R^{11}$, $R^{12}$ and $R^{13}$ are each independently a hydrogen atom, $(C_1-C_4)$alkyl, $(C_2-C_4)$alkenyl or $(C_2-C_4)$alkynyl; and X, Y and Z are each independently a hydrogen atom, halo, cyano, thiocyano or isothiocyano, provided that at least one of X, Y and Z is not a hydrogen atom; or the optical enantiomers thereof.

A third embodiment of this invention is a method for carrying out binding assays, which are useful for resistance monitoring for antitubulin drugs or pesticides to detect cells which show altered sensitivity to said antitubulin pesticides or drugs due to modifications in tubulin, comprising (i) measuring the rate of binding of an amide probe to tubulin in a test sample of eukaryotic cells, cell extracts or isolated tubulin from a cell population of unknown sensitivity to the antitubulin drug or pesticide and (ii) determining resistance as indicated by a reduction or enhancement of the rate of binding of the said amide probe to tubulin in the said test sample relative to the rate of binding of the said amide probe to tubulin in a corresponding control sample of known sensitivity to the said antitubulin drug or pesticide; said method using the said amide that binds covalently to tubulin and that inhibits the growth of eukaryotic cells, said amide having the structural formula

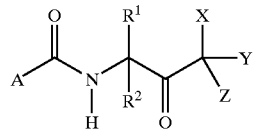

(I)

wherein

A is phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl; or phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl substituted with up to three substituents each independently selected from halo, cyano, $(C_1-C_4)$alkyl, halo$(C_1-C_4)$alkyl, $(C_2-C_4)$alkenyl, halo$(C_2-C_4)$alkenyl, $(C_2-C_4)$alkynyl, halo$(C_2-C_4)$alkynyl, $(C_1-C_4)$alkoxy, halo$(C_1-C_4)$alkoxy, $(C_1-C_4)$alkylthio, halo$(C_1-C_4)$alkylthio, nitro, —$NR^6R^7$, —$CR^8$=$NOR^9$, —$NHCOOR^{10}$, —$CONR^{11}R^{12}$, and —$COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, $(C_1-C_4)$alkyl, halo$(C_1-C_4)$alkyl, $(C_2-C_4)$alkenyl, halo$(C_2-C_4)$alkenyl, $(C_2-C_4)$alkynyl or halo$(C_2-C_4)$alkynyl, provided that both $R^1$ and $R^2$ are not a hydrogen atom;

$R^6$ and $R^7$ are each independently a hydrogen atom, $(C_1-C_4)$alkyl or $(C_1-C_4)$alkylcarbonyl;

$R^8$ is a hydrogen atom, $(C_1-C_4)$alkyl, $(C_2-C_4)$alkenyl or $(C_2-C_4)$alkynyl;

$R^9$ is a hydrogen atom, $(C_1-C_4)$alkyl, $(C_2-C_4)$alkenyl, $(C_2-C_4)$alkynyl or $(C_1-C_4)$alkylcarbonyl;

$R^{10}$, $R^{11}$, $R^{12}$ and $R^{13}$ are each independently a hydrogen atom, $(C_1-C_4)$alkyl, $(C_2-C_4)$alkenyl or $(C_2-C_4)$alkynyl; and X, Y and Z are each independently a hydrogen atom, halo, cyano, thiocyano or isothiocyano, provided that at least one of X, Y and Z is not a hydrogen atom; or the optical enantiomers thereof.

A fourth embodiment of this invention is a method for carrying out binding assays, which are useful for determination of tubulin content in eukaryotic cells, cell extracts or isolated tubulin, comprising (i) incubating the cells, cell extracts or isolated tubulin preparations of unknown tubulin content with an amide probe and (ii) comparing the rate of binding or maximum extent of binding of the said amide probe to tubulin in the sample of said unknown tubulin content with the rate of binding or maximum extent of binding of the said amide probe to tubulin in a sample of known tubulin content; said method using the said amide that binds covalently to tubulin and that inhibits the growth of eukaryotic cells, said amide having the structural formula

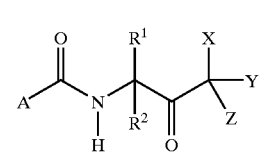

(I)

wherein

A is phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl; or phenyl, pyridyl, furyl, thienyl, isoxazolyl, oxazolyl, pyrrolyl, isothiazolyl, thiazolyl, pyrazolyl, imidazolyl, $(C_3-C_7)$cycloalkyl, pyrimidinyl, quinolyl, isoquinolyl, naphthyl, pyridazinyl, pyrazinyl, benzothienyl, indolyl, benzofuranyl or benzyl substituted with up to three substituents each independently selected from halo, cyano, $(C_1-C_4)$alkyl, halo$(C_1-C_4)$alkyl, $(C_2-C_4)$alkenyl, halo$(C_2-C_4)$alkenyl, $(C_2-C_4)$alkynyl, halo$(C_2-C_4)$alkynyl, $(C_1-C_4)$alkoxy, halo$(C_1-C_4)$alkoxy, $(C_1-C_4)$alkylthio, halo$(C_1-C_4)$alkylthio, nitro, —$NR^6R^7$, —$CR^8$=$NOR^9$, —$NHCOOR^{10}$, —$CONR^{12}$, and —$COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, $(C_1-C_4)$alkyl, halo$(C_1-C_4)$alkyl, $(C_2-C_4)$alkenyl, halo$(C_2-C_4)$alkenyl, $(C_2-C_4)$alkynyl or halo$(C_2-C_4)$alkynyl, provided that both $R^1$ and $R^2$ are not a hydrogen atom;

$R^6$ and $R^7$ are each independently a hydrogen atom, $(C_1-C_4)$alkyl or $(C_1-C_4)$alkylcarbonyl;

$R^8$ is a hydrogen atom, $(C_1-C_4)$alkyl, $(C_2-C_4)$alkenyl or $(C_2-C_4)$alkynyl;

$R^9$ is a hydrogen atom, $(C_1-C_4)$alkyl, $(C_2-C_4)$alkenyl, $(C_2-C_4)$alkynyl or $(C_1-C_4)$alkylcarbonyl;

$R^{10}$, $R^{11}$, $R^{12}$ and $R^{13}$ are each independently a hydrogen atom, $(C_1-C_4)$alkyl, $(C_2-C_4)$alkenyl or $(C_2-C_4)$alkynyl; and X, Y and Z are each independently a hydrogen atom, halo, cyano, thiocyano or isothiocyano, provided that at least one of X, Y and Z is not a hydrogen atom; or the optical enantiomers thereof.

DETAILS OF THE INVENTION

Figure 1:
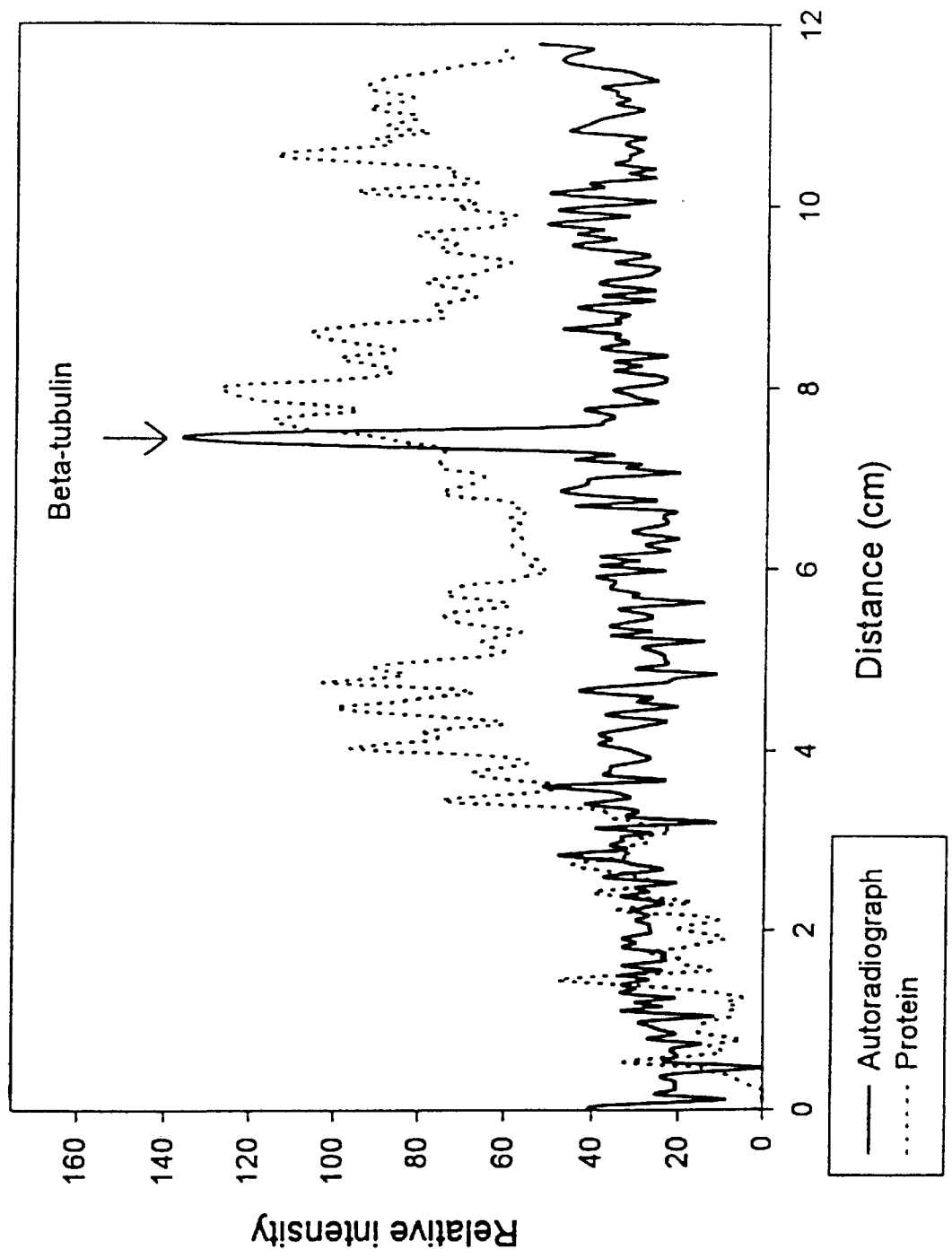
FIG. 1 depicts an analysis of radiolabeled protein by sodium dodecyl sulfate polyacrylamide gel electrophoresis and autoradiography following treatment of *Phytophthora capsici* with $^{14}$C-labeled compound 3.
Figure 2:
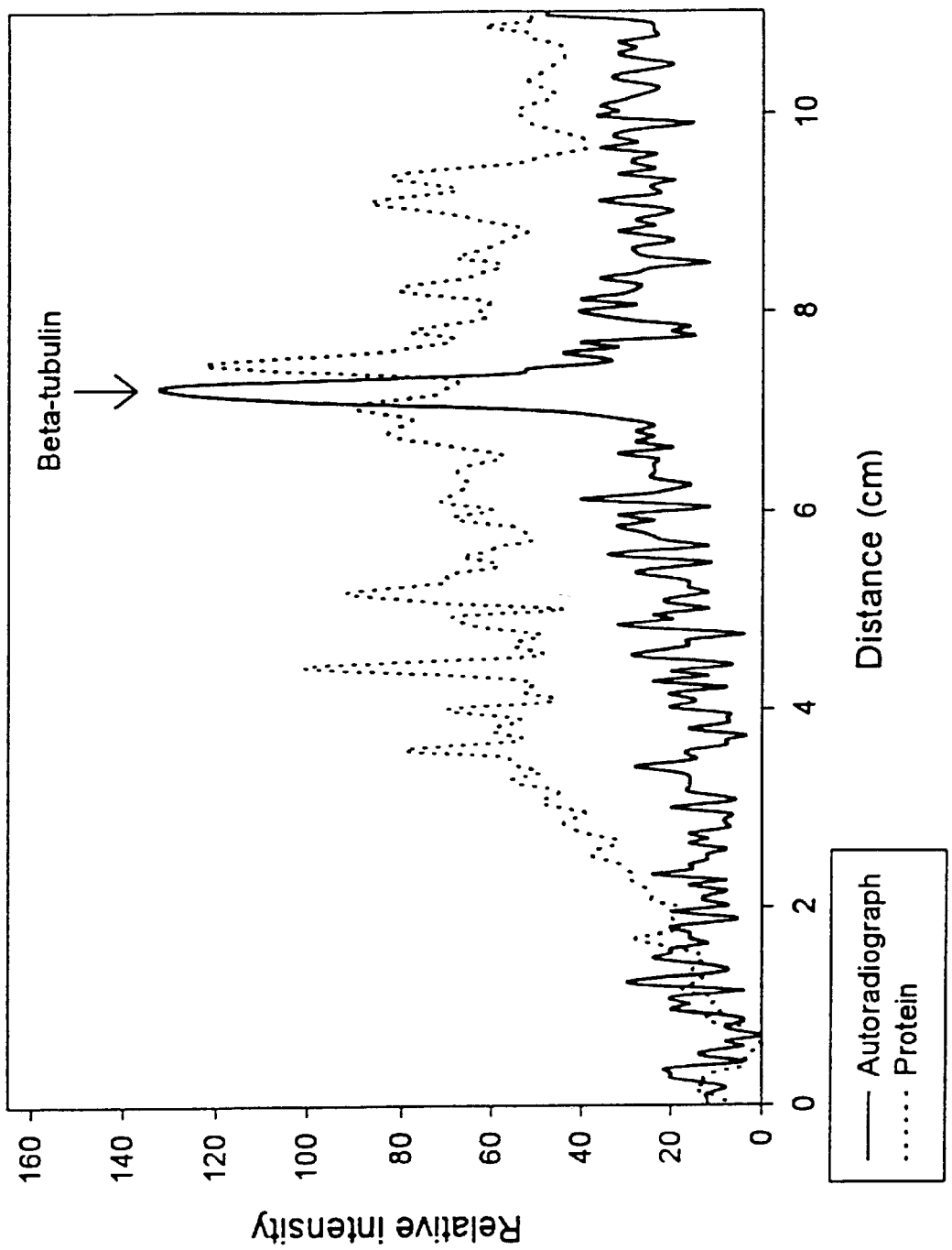
FIG. 2 depicts an analysis of radiolabeled protein by sodium dodecyl sulfate polyacrylamide gel electrophoresis and autoradiography following treatment of suspension-cultured tobacco cells with $^{14}$C-labeled compound 1.

As used herein, "halo" includes fluoro, bromo, chloro, or iodo.

"Alkyrl" includes straight or branched saturated hydrocarbon groups having from 1 to 6 carbons per group, for example, methyl, ethyl, n-propyl, isopropyl, n-butyl, isobutyl, tert-butyl, pentyl and hexyl.

"Alkenyl" includes straight or branched hydrocarbon groups having at least one double bond and from 2 to 6 carbons per group, for example, vinyl, 2-propenyl, 2-butenyl and 2-methyl-2-propenyl.

"Alkynyl" includes straight or branched hydrocarbon groups having at least one triple bond and from 2 to 6 carbons per group, for example, ethynyl, 2-propynyl and 2-butynyl.

"Alkoxy" includes straight or branched alkoxy groups having from 1 to 6 carbons per group, for example, methoxy, propoxy, n-butoxy and tert-butoxy.

"Alkylthio" includes straight or branched alkylthio groups having from 1 to 6 carbons per group, for example, methylthio and propylthio.

"Haloalkyrl", "haloalkenyl", "haloalkynyl", "haloalkoxy" and "haloalkylthio" groups are "alkyl", "alkenyl", "alkynyl", "alkoxy" and "alkylthio" groups, respectively, which have from 1 to 5 halo substituents.

"Cycloalkyl" includes cyclic rings of from 3 to 7 carbon atoms, for example, cyclopropyl, cyclopentyl and cyclohexyl.

"Alkylcarbonyl" includes straight or branched alkyl groups having from 1 to 6 carbon atoms per group which are connected to a carbonyl group, for example, methylcarbonyl and butylcarbonyl.

"Alkylsulfonyloxy" includes straight or branched alkyl groups having from 1 to 6 carbon atoms per group which are connected to a sulfonyloxy group, for example, methylsulfonyloxy and propylsulfonyloxy.

A preferred method of all four of the above embodiments uses amides having the structural formula

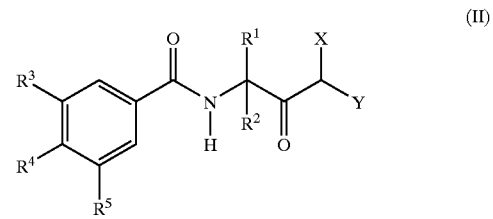

(II)

wherein $R^1$ and $R^2$ are each independently a hydrogen atom, $(C_1-C_4)$alkyl, halo$(C_1-C_4)$alkyl, $(C_2-C_4)$alkenyl or $(C_2-C_4)$alkynyl, provided that both $R^1$ and $R^2$ are not a hydrogen atom;

$R^3$, $R^4$, and $R^5$ are each independently a hydrogen atom, halo, cyano, $(C_1-C_4)$alkyl, halo$(C_1-C_4)$alkyl, $(C_2-C_4)$alkenyl, $(C_2-C_4)$alkynyl, $(C_1-C_4)$alkoxy, $(C_1-C_4)$alkylthio, halo$(C_1-C_4)$alkoxy, nitro, —$NR^6R^7$, —$CR^8$=$NOR^9$, —$NHCOOR^{10}$, —$CONR^{11}R^{12}$ or —$COOR^{13}$; or $R^4$ and $R^5$ taken together form a fused 5, 6, or 7 membered ring, which may contain up to two heteroatoms selected from the group consisting of O, S, N and P;

$R^6$, $R^7$, $R^8$, $R^9$, $R^{10}$, $R^{11}$, $R^{12}$, and $R^{13}$ are each independently a hydrogen atom or $(C_1-C_4)$alkyl; and X and Y are each independently a hydrogen atom, halo, cyano, thiocyano or isothiocyano, provided that both X and Y are not a hydrogen atom; or the optical enantiomers thereof.

A more preferred method uses benzoic acid amides having the structural formula (II) wherein $R^1$ is methyl;

$R^2$ is methyl or ethyl;

$R^3$ and $R^5$ are each independently a hydrogen atom, halo, methyl, nitro, cyano, —$NR^6R^7$, —$CR^8$=$NOR^9$ or —$NHCOOR^{10}$, provided that both $R^3$ and $R^5$ are not a hydrogen atom;

$R^4$ is a hydrogen atom, halo, —$NR^6R^7$, cyano, —$CR^8$=$NOR^9$, —$NHCOOR^{10}$, —$COOR^{13}$, or $(C_1-C_4)$alkyl;

$R^6$, $R^7$, $R^8$, $R^9$, $R^{10}$ and $R^{13}$ are each independently a hydrogen atom or $(C_1-C_4)$alkyl;

X is chloro; and

Y is a hydrogen atom; or the optical enantiomers thereof.

An even more preferred method, used in assays employing mammalian cells, cell extracts or tubulin, uses benzoic acid amides having the structural formula (II) wherein $R^1$ is methyl, $R^2$ is ethyl, $R^3$ is halo or cyano, $R^4$ and $R^5$ are amino or —CH=$NOCH_3$ provided that $R^4$ and $R^5$ are not the same, X is chloro, and Y is a hydrogen atom; or the optical enantiomers thereof.

A second even more preferred method, used in assays employing fungal cells, cell extracts or tubulin in which the fungus belongs to the Ascomycete, Deuteromycete or Basidiomycete classes of fungi, uses benzoic acid amides having the structural formula (II) wherein $R^1$ is methyl, $R^2$ is methyl or ethyl, $R^3$ is —CH=NOCH$_3$, $R^4$ is a hydrogen atom, halo, amino, cyano or methyl, $R^5$ is halo, methyl, nitro or cyano, X is chloro and Y is a hydrogen atom; or the optical enantiomers thereof.

A third even more preferred method, used in assays employing fungal cells, cell extracts or tubulin in which the fungus belongs to the Oomycete class of fungi, uses benzoic acid amides having the structural formula (II) wherein $R^1$ is methyl, $R^2$ is ethyl, $R^3$ and $R^5$ are each independently a hydrogen atom, halo, methyl, nitro, cyano, —NR$^6$R$^7$, —CR$^8$=NOR$^9$ or —NHCOOR$^{10}$, provided that both $R^3$ and $R^5$ are not a hydrogen atom, $R^4$ is a hydrogen atom, halo, —NR$^6$R$^7$, cyano, —CR$^8$=NOR$^9$, —NHCOOR$^{10}$, —COOR$^{13}$ or (C$_1$–C$_4$)alkyl, $R^6$, $R^7$, $R^8$, $R^9$, $R^{10}$ and $R^{13}$ are each independently a hydrogen atom or methyl, X is chloro, and Y is a hydrogen atom; or the optical enantiomers thereof.

A fourth even more preferred method, used in assays employing plant cells, cell extracts or tubulin, uses benzoic acid amides having the structural formula (II) wherein $R^1$ is methyl, $R^2$ is methyl or ethyl, $R^3$ and $R^5$ are each independently a hydrogen atom, halo, methyl, nitro or cyano, provided that both $R^3$ and $R^5$ are not a hydrogen atom, $R^4$ is a hydrogen atom, X is chloro, and Y is a hydrogen atom; or the optical enantiomers thereof.

A second more preferred method of all four of the above embodiments uses pyridinecarboxamides having the structural formula (III)

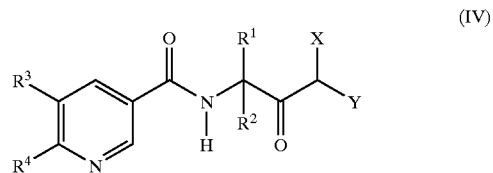

wherein $R^1$ and $R^2$ are each independently a hydrogen atom, (C$_1$–C$_4$)alkyl, halo(C$_1$–C$_4$)alkyl, (C$_2$–C$_4$)alkenyl or (C$_2$–C$_4$)alkynyl, provided that both $R^1$ and $R^2$ are not a hydrogen atom;

$R^3$ and $R^5$ are each independently a hydrogen atom, halo, cyano, (C$_1$–C$_4$)alkyl, halo(C$_1$–C$_4$)alkyl, (C$_2$–C$_4$)alkenyl, (C$_2$–C$_4$)alkynyl, (C$_1$–C$_4$)alkoxy, —NHCOOR$^{10}$, —CONR$^{11}$R$^{12}$ or —COOR$^{13}$;

$R^6$, $R^7$, $R^8$, $R^9$, $R^{10}$, $R^{11}$, $R^{12}$, and $R^{13}$ are a hydrogen atom or (C$_1$–C$_4$)alkyl; and X and Y are each independently a hydrogen atom, halo, cyano, thiocyano or isothiocyano, provided that both X and Y are not a hydrogen atom; or the optical enantiomers thereof.

A third more preferred method of all four of the above embodiments uses pyridinecarboxamides having the structural formula (IV)

wherein $R^1$ and $R^2$ are each independently a hydrogen atom, (C$_1$–C$_4$)alkyl, halo(C$_1$–C$_4$)alkyl, (C$_2$–C$_4$)alkenyl or (C$_2$–C$_4$)alkynyl, provided that both $R^1$ and $R^2$ are not a hydrogen atom;

$R^3$ and $R^4$ are each independently a hydrogen atom, halo, cyano, (C$_1$–C$_4$)alkyl, halo(C$_1$–C$_4$)alkyl, C$_2$–C$_4$) alkenyl, (C$_2$–C$_4$)alkynyl, (C$_1$–C$_4$)alkoxy, (C$_1$–C$_4$) alkylthio, halo(C$_1$–C$_4$)alkoxy, nitro, carboxy, —NR$^6$R$^7$, —CR$^8$=NOR$^9$, —NHCOOR$^{10}$, —CONR$^{11}$R$^{12}$ or —COOR$^{13}$; or $R^3$ and $R^4$ taken together may form a fused 5, 6 or 7 membered ring which may contain up to two heteroatoms selected from the group consisting of: O, S, N, and P;

$R^6$, $R^7$, $R^8$, $R^9$, $R^{10}$, $R^{11}$, $R^{12}$ and $R^{13}$ are each independently a hydrogen atom or (C$_1$–C$_4$)alkyl; and X and Y are each independently a hydrogen atom, halo, cyano, thiocyano or isothiocyano, provided that both X and Y are not a hydrogen atom; or the optical enantiomers thereof.

An even more preferred method uses pyridinecarboxamides having the structural formula (IV) wherein $R^1$ is methyl;

$R^2$ is methyl or ethyl;

$R^3$ and $R^4$ are each independently a hydrogen atom, halo, cyano, methyl, nitro, —NR$^6$R$^7$, —CR$^8$=NOR$^9$ or —NHCOOR$^{10}$, provided that both $R^3$ and $R^4$ are not a hydrogen atom;

$R^6$, $R^7$, $R^8$, $R^9$, $R^{10}$ and $R^{13}$ are each independently a hydrogen atom or (C$_1$–C$_4$)alkyl;

X is chloro and Y is a hydrogen atom; or the optical enantiomers thereof.

A fourth more preferred method of all four of the above embodiments uses furylcarboxamides or thienylcarboxamides having the structural formula

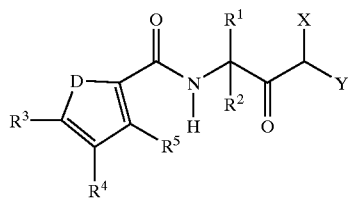

wherein

D is O or S;

R[1] and R[2] are each independently a hydrogen atom, $(C_1-C_4)$alkyl, halo$(C_1-C_4)$alkyl, $(C_2-C_4)$alkenyl, and $(C_2-C_4)$alkynyl, provided that both R[1] and R[2] are not a hydrogen atom;

R[3], R[4], and R[5] are each independently a hydrogen atom, halo, cyano, $(C^1-C_4)$alkyl, halo$(C^1-C_4)$alkyl, $(C_2-C_4)$alkenyl, $(C_2-C_4)$alkynyl, $(C_1-C_4)$alkoxy, $(C_1-C_4)$alkylthio, halo$(C_1-C_4)$alkoxy, nitro, carboxy, —NR[6]R[7], —CR[8]=NOR[9], —NHCOOR[10], —CONR[11]R[12] or —COOR[13]; or R[3] and R[4] taken together may form a fused 5, 6 or 7 membered ring which may contain up to two heteroatoms selected from the group consisting of O, S, N, and P;

R[6], R[7], R[8], R[9], R[10], R[11], R[12], and R[13] are each independently a hydrogen atom or $(C_1-C_4)$alkyl; and X and Y are each independently a hydrogen atom, halo, cyano, thiocyano or isothiocyano, provided that both X and Y are not a hydrogen atom; or the optical enantiomers thereof.

A fifth more preferred method of all four of the above embodiments uses furylcarboxamides or thienylcarboxamides having the structural formula

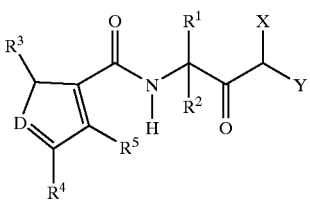

wherein

D is O or S;

R[1] and R[2] are each independently a hydrogen atom, $(C_1-C_4)$alkyl, halo$(C_1-C_4)$alkyl, $(C_2-C_4)$alkenyl, and $(C_2-C_4)$alkynyl, provided that both R[1] and R[2] are not a hydrogen atom;

R[3], R[4], and R[5] are each independently a hydrogen atom, halo, cyano, $(C_1-C_4)$alkyl, halo$(C_1-C_4)$alkyl, $(C_2-C_4)$alkenyl, $(C_2-C_4)$alkynyl, $(C_1-C_4)$alkoxy, $(C_1-C_4)$alkylthio, halo$(C_1-C_4)$alkoxy, nitro, carboxy, —NR[6]R[7], —CR[8]=NOR[9], —NHCOOR[10], —CONR[11]R[12] or —COOR[13];

R[6], R[7], R[8], R[9], R[10], R[11], R[12] and R[13] are each independently a hydrogen atom or $(C_1-C_4)$alkyl; and X and Y are each independently a hydrogen atom, halo, cyano, thiocyano or isothiocyano, provided that both X and Y are not a hydrogen atom; or the optical enantiomers thereof.

When R[1] and R[2] are different, optical enantiomers of the compounds of the present invention are possible due to the presence of an asymmetric carbon atom linking R[1] and R[2]. In such cases, both enantiomers are within the scope of the present invention. It is known that many biologically active compounds have optical enantiomers, one of which may bind more effectively to a particular protein than the other. Similarly, for compounds used in the methods of the present invention, one enantiomer may bind more effectively to tubulin than the other enantiomer. For example, the "S enantiomers" of compounds 1, 2 and 3 bind more effectively to tubulin than the corresponding "R enantiomers". The term "S enantiomer" means that the four groups on the carbon to which R[1] and R[2] are attached, when ranked according to the set of sequence rules of the Cahn-Ingold-Prelog system {*Angew. Chem. Int. Ed. Engl.* 5, 385–415 (1966)}, define the carbon as having an S configuration. The term "R enantiomer" means that the four groups form an R configuration.

Particular compounds which have been made and which are expected to be useful in the method of the present invention include, but are not limited to, those compounds listed in Tables 1–6.

TABLE 1

Benzoic Acid Amides of Formula (II)

| Compound | R[1] | R[2] | R[3] | R[4] | R[5] | X | Y |
|---|---|---|---|---|---|---|---|
| 1 | CH$_3$ | C$_2$H$_5$ | Cl | H | Cl | Cl | H |
| 2 | CH$_3$ | C$_2$H$_5$ | CH=NOCH$_3$ | NH$_2$ | Cl | Cl | H |
| 3 | CH$_3$ | C$_2$H$_5$ | Cl | CH$_3$ | Cl | Cl | H |
| 4 | CH$_3$ | C$_2$H$_5$ | H | NHCOOCH$_3$ | H | Cl | H |
| 5 | CH$_3$ | C$_2$H$_5$ | Cl | NH$_2$ | Cl | Cl | H |
| 6 | CH$_3$ | C$_2$H$_5$ | CN | H | Cl | Cl | H |
| 7 | CH$_3$ | C$_2$H$_5$ | CH=NOCH$_3$ | H | Cl | Cl | H |
| 8 | CH$_3$ | C$_2$H$_5$ | Br | H | CH$_3$ | Cl | H |
| 9 | CH$_3$ | C$_2$H$_5$ | Cl | H | Cl | Br | Br |
| 10 | CH$_3$ | CH$_3$ | Cl | H | Cl | Br | Cl |
| 11 | CH$_3$ | CH$_3$ | Cl | H | Cl | Br | Br |
| 12 | CH$_3$ | C$_2$H$_5$ | Br | NH$_2$ | Br | Cl | H |
| 13 | CH$_3$ | C$_2$H$_5$ | CN | H | H | Cl | H |
| 14 | CH$_3$ | C$_2$H$_5$ | Br | CH$_3$ | Br | Cl | H |
| 15 | CH$_3$ | C$_2$H$_5$ | CN | H | CH$_3$ | Cl | H |
| 16 | CH$_3$ | C$_2$H$_5$ | CH=NOCH$_3$ | H | H | Cl | H |

TABLE 1-continued

Benzoic Acid Amides of Formula (II)

| Compound | R¹ | R² | R³ | R⁴ | R⁵ | X | Y |
|---|---|---|---|---|---|---|---|
| 17 | $CH_3$ | $C_2H_5$ | Cl | H | Cl | SCN | H |
| 18 | $CH_3$ | $CH_3$ | Cl | H | Cl | NCS | H |
| 19 | $CH_3$ | $CH_3$ | Cl | H | Cl | Cl | H |
| 20 | $CH_3$ | $CH_3$ | Cl | H | Cl | Br | H |
| 21 | $CH_3$ | $C_2H_5$ | Br | $CH_3$ | Cl | Cl | H |
| 22 | $CH_3$ | $C_2H_5$ | Cl | F | Cl | Cl | H |
| 23 | $CH_3$ | $C_2H_5$ | Cl | Cl | Cl | Cl | H |
| 24 | $CH_3$ | $C_2H_5$ | F | H | F | Cl | H |
| 25 | $CH_3$ | $C_2H_5$ | Cl | H | H | Cl | H |
| 26 | $CH_3$ | $C_2H_5$ | F | F | F | Cl | H |
| 27 | $CH_3$ | $CH(CH_3)_2$ | Cl | H | Cl | Cl | H |
| 28 | $CH_3$ | $C_2H_5$ | Cl | H | Cl | F | Br |
| 29 | $CH_3$ | $CH_3$ | Cl | H | Cl | Cl | Cl |
| 30 | $CH_3$ | $C_2H_5$ | $NHCOOCH_3$ | H | H | Cl | H |

TABLE 2

Pyridine Carboxamides of Formula (III)

| Compound | R¹ | R² | R³ | R⁵ | X | Y |
|---|---|---|---|---|---|---|
| 31 | $CH_3$ | $CH_3$ | Cl | Cl | Br | Br |
| 32 | $CH_3$ | $CH_3$ | Cl | Cl | Cl | H |

TABLE 3

Pyridine Carboxamides of Formula (IV)

| Compound | R¹ | R² | R³ | R⁴ | X | Y |
|---|---|---|---|---|---|---|
| 33 | $CH_3$ | $C_2H_5$ | Br | H | Cl | H |
| 34 | $CH_3$ | $C_2H_5$ | H | Cl | Cl | H |

TABLE 4

Thienylcarboxamides and Furylcarboxamide of Formula (V)

| Compound | D | R¹ | R² | R³ | R⁴ | R⁵ | X | Y |
|---|---|---|---|---|---|---|---|---|
| 35 | S | $CH_3$ | $CH_3$ | Br | Br | H | Cl | H |
| 36 | S | $CH_3$ | $C_2H_5$ | $CH_3$ | H | H | Cl | H |
| 37 | S | $CH_3$ | $CH_3$ | H | H | H | Br | Br |
| 38 | O | $CH_3$ | $C_2H_5$ | Br | H | H | Br | Br |

TABLE 5

Thienylcarboxamide of Formula (VI)

| Compound | D | R¹ | R² | R³ | R⁴ | R⁵ | X | Y |
|---|---|---|---|---|---|---|---|---|
| 39 | S | $CH_3$ | $CH_3$ | Cl | Cl | H | Cl | H |

TABLE 6

Fused Ring Benzoic Acid Amides of Formula (II)

| Compound | R¹ | R² | R³ | R⁴R⁵ * | X | Y |
|---|---|---|---|---|---|---|
| 40 | $CH_3$ | $C_2H_5$ | H | —N=CH—O— | Cl | H |
| 41 | $CH_3$ | $C_2H_5$ | H | —O—CH=N— | Cl | H |
| 42 | $CH_3$ | $C_2H_5$ | H | —N=CH—S— | Cl | H |

TABLE 6-continued

Fused Ring Benzoic Acid Amides of Formula (II)

| Compound | R¹ | R² | R³ | R⁴R⁵ * | X | Y |
|---|---|---|---|---|---|---|
| 43 | $CH_3$ | $C_2H_5$ | Cl | —N=CH—O— | Cl | H |
| 44 | $CH_3$ | $C_2H_5$ | Cl | —N=C($CH_3$)—O— | Cl | H |

* The left hand most atom is attached to the 4-position of the benzoic acid amide ring and the right hand most atom is attached to the 5-position of the benzoic acid amide ring.

The following methods and examples further illustrate the use of the present invention.

Methods Used in Preparing Compounds Listed in Tables 1–6

Compounds 1, 6, 8, 9, 10, 11, 13, 15, 17, 18, 19, 20, 22, 23, 24, 25, 26, 27, 28 and 29 in Table 1

Compounds 1, 6, 8, 9, 10, 11, 13, 15, 17, 18, 19, 20, 22, 23, 24, 25, 26, 27, 28 and 29 in Table 1 were prepared according to synthetic methods described in U.S. Pat. No. 4,822,902, columns 5–8 and 11–17.

Compounds 7 and 16 in Table 1

Compounds 7 and 16 in Table 1 were prepared according to synthetic methods described in U.S. Pat. No. 5,254,584, columns 7 and 8 (compound 16) and 10–14 (compound 7).

Compounds 3, 14 and 21 in Table 1

Compounds 3, 14 and 21 were prepared according to synthetic methods described in U.S. Pat. No. 5,304,572, columns 4–8.

Compounds 5 and 12 in Table 1

Compounds 5 and 12 were prepared using conventional synthesis techniques, as described for example in U.S. Pat. No. 4,863,940, columns 5–7, from appropriate benzoic acids or benzoyl chlorides. Thus, compounds 5 and 12 were prepared using 4-amino-3,5-dichlorobenzoylchloride and 4-amino-3,5-dibromobenzoylchloride, respectively.

Compound 2 in Table 1

Compound 2 was prepared by reaction of the benzoyl chloride VII, in which R³ is Cl, R⁴ is $NH_2$ and R⁵ is —CH=$NOCH_3$, with the α-amino-α'-chloroketone derivative VIII, in which R¹ is methyl and R² is ethyl, as illustrated in Scheme A:

Scheme A

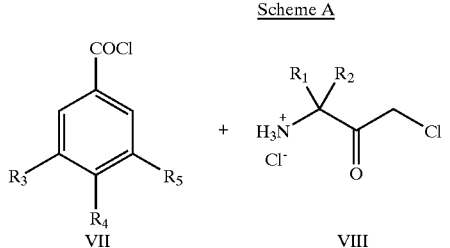

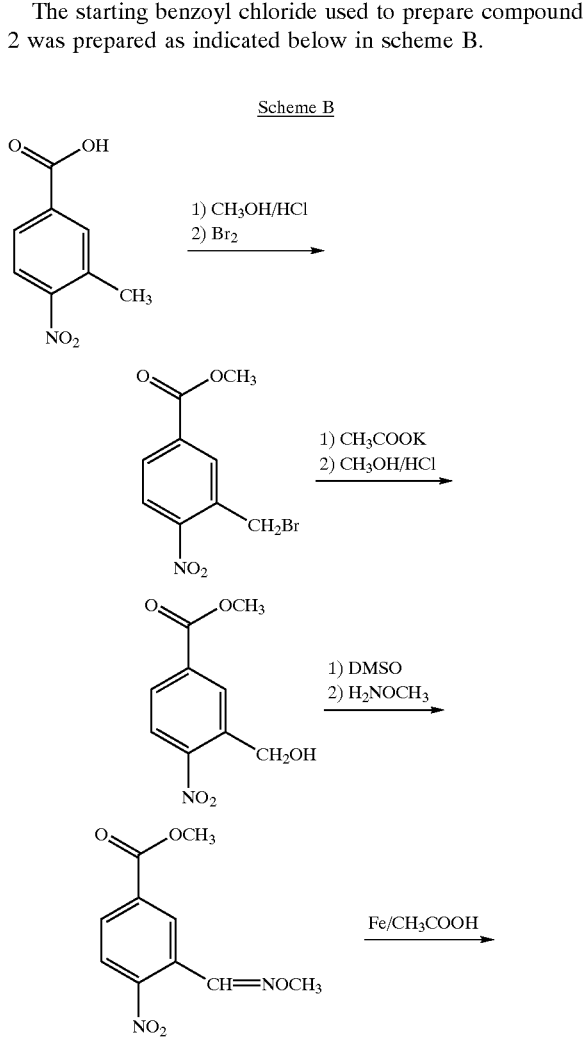

The starting benzoyl chloride used to prepare compound 2 was prepared as indicated below in scheme B.

Scheme B

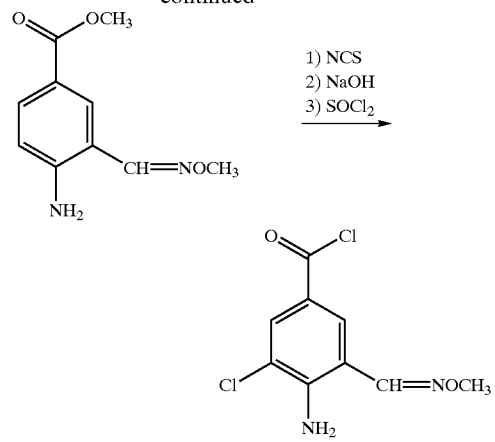

Compound VIII was prepared by treating the acetylenic amine (X) with trifluoracetic anhydride in the presence of a solvent such as methylene chloride, chloroform, ethyl ether, or water and a base such as triethylamine, sodium carbonate, sodium bicarbonate, or sodium hydroxide to yield the acetylenic amide XI:

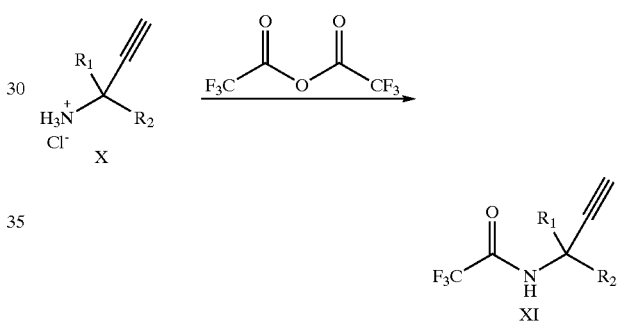

Treatment of the acetylenic amide XI with chlorine or a chlorine source at a temperature of from −78° C. to 0° C. in the presence of a solvent such as methylene chloride or chloroform yielded the intermediate oxazoline (XII). The oxazoline XII was readily hydrolyzed under acidic conditions using an acid such as hydrochloric acid or sulfuric acid with a solvent such as methanol or tetrahydrofuran at a temperature of from 40° C. to 60° C., and yielded the α-amino-α',α'-dichloroketone (XIII).

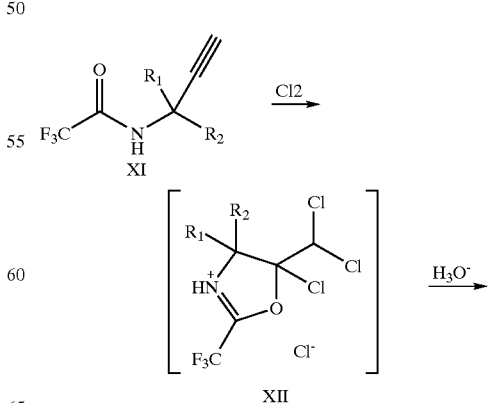

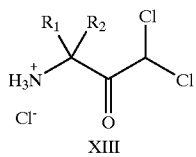

Selective catalytic dehalogenation of XIII yielded the respective α-amino-α'-chloroketone derivative VIII:

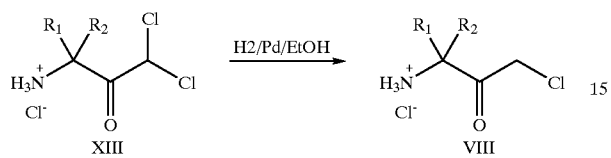

a) Preparation of methyl 3-methyl-4-nitrobenzoate

In a 5-liter three-necked round-bottomed flask equipped with a reflux condenser, overhead stirrer and gas inlet, was placed 300 g of 3-methyl-4-nitrobenzoic acid and 3 l of methanol. To the resulting well-stirred solution was bubbled in 20.8 g of hydrogen chloride and the resulting mixture was refluxed for 3 hours. The reaction mixture was cooled to room temperature and allowed to stand overnight. The expected methyl 3-methyl-4-nitrobenzoate precipitated as light yellow crystals, which were collected by suction filtration yielding after drying 259.3 g. This solid was used as such in the next step.

b) Preparation of methyl 3-bromomethyl-4-nitrobenzoate

In a 5-liter three-necked round-bottomed flask equipped with a reflux condenser, overhead stirrer, addition funnel and nitrogen inlet, was placed 220 g of methyl 3-methyl-4-nitrobenzoate, 2 l of anhydrous carbon tetrachloride and 4 g of benzoyl peroxide. To the resulting solution, irradiated with a 275 watt UV light, was added 198 g of bromine dropwise over a period of 2 hours at reflux. After the addition was complete the reaction mixture was refluxed for an additional 60 hours. The reaction mixture was cooled to room temperature. The solid which formed was separated by suction filtration. This solid (159.1 g) consisted of the expected methyl 3-bromomethyl-4-nitrobenzoate with minor amounts of the starting material. The mother liquors together with another 220 g of methyl 3-methyl-4-nitrobenzoate and 4 g of benzoyl peroxide were returned to the flask and treated with 198 g of bromine as described above. After the addition was complete the reaction mixture was refluxed another 96 hours, cooled to room temperature and the resulting solid separated by filtration yielding another 252 g of methyl 3-bromomethyl-4-nitrobenzoate. The solids were combined yielding a total of 411.1 g of methyl 3-bromomethyl-4-nitrobenzoate with minor amounts of the starting methyl 3-methyl-4-nitrobenzoate and methyl 3-dibromomethyl-4-nitrobenzoate. This solid was used as such in the next step.

c) Preparation of methyl 3-acetoxymethyl-4-nitrobenzoate

In a 5-liter three-necked round-bottomed flask equipped with a reflux condenser, overhead stirrer and nitrogen inlet, was placed 411 g of the previously prepared methyl 3-bromomethyl-4-nitrobenzoate, 441 g of anhydrous potassium acetate and 2 l of glacial acetic acid. The resulting mixture was refluxed for 4 hours, cooled to room temperature and stirred overnight. The solvent was removed in a rotary evaporator and the resulting light yellow solid treated with a mixture of 2 l of ethyl acetate and 1 l of water. The organic phase was separated, washed with water (3×400 mL), brine (1×400 mL) dried over anhydrous magnesium sulfate and the solvent removed using a rotary evaporator. The crude reaction mixture was triturated with hexane and filtered yielding 318 g of the expected methyl 3-acetoxymethyl-4-nitrobenzoate. This compound was used as such in the next step.

d) Preparation of methyl 3-hydroxymethyl-4-nitrobenzoate

In a 5-liter three-necked round-bottomed flask equipped with a reflux condenser, overhead stirrer and nitrogen inlet, was placed 318 g of the previously prepared methyl 3-acetoxymethyl-4-nitrobenzoate and 3.2 l of anhydrous methanol. To the resulting solution was bubbled in 40 g of hydrogen chloride and the resulting mixture was refluxed for 3 hours. After cooling to room temperature the solvent was removed using a rotary evaporator yielding 273 g of methyl 3-hydroxymethyl-4-nitrobenzoate as a yellow solid containing traces of methanol, which was used as such in the next step.

e) Preparation of methyl 3-formyl-4-nitrobenzoate

In a 5-liter four-necked round-bottomed flask 1.5 l of methylene chloride was cooled to −78° C. Oxalyl chloride (164 g, 1.29 moles) was added slowly, followed by dropwise addition of 202 g (2.59 moles) of dry dimethylsulfoxide in 125 mL of methylene chloride, keeping the temperature below −70° C. After the addition was complete the reaction mixture was stirred at −78° C. for 30 minutes and 273 g (1.29 moles) of previously prepared methyl 3-hydroxymethyl-4-nitrobenzoate dissolved in 250 mL of methylene chloride was added dropwise. The reaction mixture was stirred an additional 30 minutes. Triethylamine (392 g 3.88 moles) in 125 mL of methylene chloride was added dropwise keeping the temperature below −65° C. The reaction mixture was warmed up slowly to room temperature and stirred overnight. The solvent was removed using a rotary evaporator and the resulting solid treated with a mixture of 2 l of ethyl acetate and 1 l of water. The organic phase was separated, filtered through diatomaceous earth, and washed sequentially with dilute aqueous hydrochloric acid (2×250 mL), water (2×250 mL), saturated aqueous sodium bicarbonate (2×250 mL), water (2×200 mL), brine (1×200 mL) and dried over anhydrous magnesium sultate. The solvent was removed using a rotary evaporator. The crude reaction mixture was triturated with hexane and filtered yielding 234.1 g of the expected methyl 3-formyl-4-nitrobenzoate as a yellow solid. This compound was used as such in the next step.

f) Preparation of methyl 3-methoxyiminomethyl-4-nitrobenzoate

To a well stirred mixture of 195 g of methyl 3-formyl-4-nitrobenzoate, 1 l methylene chloride and 370 mL of water was added sequentially 77.6 g of methoxyamine hydrochloride, 76.2 g of sodium acetate and 6.8 g of tetra-n-butylammonium hydrogen sulfate. The resulting mixture was stirred overnight at room temperature, then diluted with 2 l of ethyl ether. The organic phase was separated and washed sequentially with water (1×500 mL), 2% aqueous hydrochloric acid (2×500 mL), water (2×250 mL), and brine (1×250 mL); then dried over anhydrous magnesium sulfate. The solvent was removed using a rotary evaporator yielding 218.6 g of the expected methyl 3-methoxyiminomethyl-4-nitrobenzoate as a reddish oil that solidified upon standing, and which was used as such in the next step.

g) Preparation of methyl 4-amino-3-methoxyiminomethylbenzoate

In a 5-liter three-necked round-bottomed flask was placed 0.9 l of 5% aqueous acetic acid and 157 g (2.8 moles) of iron. To the resulting well-stirred mixture was added 166.6 g (0.7 moles) of the previously prepared methyl 3-methoxyiminomethyl-4-nitrobenzoate dissolved in 0.9 l of ethyl acetate followed by dropwise addition of 0.9 l of acetic acid while keeping the temperature below 35 C. The resulting mixture was stirred at 35° C. for 30 minutes and filtered through diatomaceous earth. The filtrate was poured into 5 l of water. The aqueous phase was separated and washed with ethyl ether (2×500 mL). The combined organic layers were washed sequentially with water (4×500 mL), saturated aqueous sodium bicarbonate (2×500 mL), water (2×500 mL), and brine (1×400 mL). The organic layer was dried over anhydrous magnesium sulfate and the solvent removed using a rotary evaporator yielding 130 g of the expected methyl 4-amino-3-methoxyiminomethylbenzoate.

h) Preparation of methyl 4-amino-3-chloro-5-methoxyiminomethylbenzoate

In a 2-liter three-necked round-bottomed flask was placed 106 g (0.51 moles) of the previously prepared 4-amino-3-methoxyiminomethylbenzoate and 500 mL of acetonitrile. The resulting mixture was heated at 70° C. and 75.2 g (0.56 moles) of N-chlorosuccinimide was added portionwise while keeping the temperature below 80° C. After the addition was complete the reaction mixture was refluxed for 1 hour. The reaction mixture was cooled to room temperature and the solvent eliminated in a rotary evaporator. The crude product was dissolved in 5 l of ethyl acetate. The organic solution was washed with water (3×500 mL) and then brine, dried over magnesium sulfate. The reaction mixture was concentrated in a rotary evaporator to a slurry, triturated with hexane and filtered yielding the expected methyl 4-amino-3-chloro-5-methoxyiminomethylbenzoate as a yellow solid. This reaction was repeated using the same amounts yielding a total of 210.5 g of methyl 4-amino-3-chloro-5-methoxyiminomethylbenzoate, which was used as such in the next step.

i) Preparation of 4-amino-3-chloro-5-methoxyiminomethylbenzoic acid

In a 5-liter three-necked round-bottomed flask was placed 210 g (0.86 moles) of the previously prepared 4-amino-3-chloro-5-methoxyiminomethylbenzoate, 1.7 l of methanol and 462 g (1.73 moles) of 15% aqueous sodium hydroxide. The resulting mixture was refluxed for 3 hours, after which the reaction mixture was stirred overnight at room temperature. The reaction mixture was concentrated using a rotary evaporator. The crude reaction mixture was dissolved in 2 l of water. The resulting aqueous solution was washed once with 500 mL of ethyl acetate, cooled in an ice bath and acidified to pH=2 with concentrated hydrochloric acid. The expected 4-amino-3-chloro-5-methoxyiminomethylbenzoic acid precipitated as a light yellow solid which was separated by suction filtration. The filter cake was washed with a 1:2 mixture of ethyl ether and hexane yielding after drying 185.2 g (94% yield).

j) Preparation of 4-amino-3-chloro-5-methoxyiminomethylbenzoyl chloride

In a 5-liter three-necked round-bottomed flask was placed 180 g of the previously prepared 4-amino-3-chloro-5-methoxyiminomethylbenzoic acid, 2 l of toluene, 3 mL of dimethylformamide and 104 g (64 mL) of thionyl chloride. The resulting mixture was heated at 70° C. for 2 hours, filtered while hot and the solvent removed using a rotary evaporator yielding 178.1 g of the expected 4-amino-3-chloro-5-methoxyiminomethylbenzoyl chloride.

k) Preparation of 3-amino-1-chloro-3-methyl-2-pentanone hydrochloride (Compound VIII, Wherein $R^1$ is Methyl and $R^2$ is Ethyl)

(i) Preparation of N-[3-(3-methyl-1-pentynyl)]trifluoroacetamide

In a 3 liter, four-necked, round-bottomed flask fitted with a mechanical stirrer, nitrogen inlet and thermometer was placed 234 grams (g) (1.75 mole) of 3-amino-3-methyl-1-pentynyl hydrochloride and 1,000 mL of methylene chloride. To the resulting well-stirred mixture was added slowly 354 g (3.51 mole) of triethylamine (TEA) dropwise, keeping the temperature below 30° C. After the addition was completed, the reaction mixture was stirred 120 minutes followed by dropwise addition of 334.5 g (1.59 mole) of trifluoroacetic anhydride dissolved in 500 mL of methylene chloride at such a rate to keep the reaction temperature at 0° C. After the addition was completed the reaction mixture was stirred at room temperature overnight and concentrated in vacuo. The resulting slurry was washed with ethyl ether. The ethyl ether layer was washed sequentially with water, saturated aqueous sodium bicarbonate and brine, dried over anhydrous magnesium sulfate, treated with activated charcoal, and filtered through Celite™. The solvent was eliminated under reduced pressure. The resulting crude product was treated with cold pentane, filtered, and dried yielding 255.5 g (83%) of the expected N-[3-(3-methyl-1-pentynyl)]trifluoroacetamide as a white solid.

(ii) Preparation of 5-chloro-5-(dichloromethyl)-4-ethyl-4-methyl-2-trifluoromethyloxazoline hydrochloride In a 5 L, four-necked, round-bottomed flask fitted with a mechanical stirrer, a thermometer, and a gas inlet was dissolved 255.5 g (1.32 mole) of N-[3-(3-methyl-1-pentynyl)]trifluoroacetamide in 4,000 mL of methylene chloride. The resulting mixture was cooled to −30° C. and 235 g of chlorine was bubbled in over a 2 hour period. When the addition was completed the reaction mixture was stirred at −30° C. during 30 minutes and warmed to room temperature. The crude reaction mixture was evaporated in the rotary evaporator yielding the expected 5-chloro-5-(dichloromethyl)-4-ethyl-4-methyl-2-trifluoromethyloxazoline hydrochloride which was used as such in the next step.

(iii) Preparation of 3-amino-1,1-dichloro-3-methyl-2-pentanone hydrochloride The 5-chloro-5-(dichloromethyl)-4-ethyl-4-methyl-2-trifluoromethyloxazoline hydrochloride prepared in the preceding step was dissolved in 1800 mL of methanol, 72 mL of water, and 190 mL of concentrated hydrochloric acid, warmed to 50° C., and stirred at that temperature overnight. The crude reaction mixture was cooled and poured into an ice/water/ethyl ether mixture. The phases were separated and the ether layer was extracted once with water. The ether was saved (organic I). The combined aqueous layers were washed once with ethyl ether, and the organic layer was combined with organic I (organic II). The aqueous layer was neutralized with saturated aqueous sodium bicarbonate and extracted twice with ethyl ether. The combined ether layers were washed with water, brine, dried over anhydrous magnesium sulfate, treated with activated charcoal, and filtered through Celite™. To the resulting colorless solution was bubbled in anhydrous hydrogen chloride keeping the temperature below 20° C. The resulting white solid was filtered and dried yielding 124.8 g of the expected 3-amino-1,1-dichloro-3-methyl-2-pentanone hydrochloride as a white solid. The ethyl ether filtrate was combined with organic II and concentrated in vacuo; the resulting residue (150 g) was taken in a mixture of methanol/water/concentrated hydrochloric acid and heated at 50° C. over the weekend. The previously described workup yielded another 51 g of 3-amino-1,1-dichloro-3-methyl-2-pentanone hydrochloride. The total amount obtained was 175.8 g (61% yield).

(iv) Preparation of 3-amino-1-chloro-3-methyl-2-pentanone hydrochloride

In a 2 L Parr™ bottle was placed 41 g of 3-amino-1,1-dichloro-3-methyl-2-pentanone hydrochloride, 0.8 g of 10% palladium over charcoal, and 400 mL of ethanol. The resulting mixture was shaken in a Parr™ apparatus at 50 psi for 3 hours. The crude reaction mixture was filtered through Celite™ and evaporated in vacuo yielding a viscous oil, which was taken in 300 to 400 mL of ethyl acetate and stirred at room temperature for several hours. The expected 3-amino-1-chloro-3-methyl-2-pentanone hydrochloride crystallized as a white solid; 300 mL of hexane was added to the resulting suspension and filtered yielding 34 g (98%) of the expected 3-amino-1-chloro-3-methyl-2-pentanone hydrochloride.

The reaction was repeated starting with 41 g; 41 g; and 51 g of 3-amino-1,1-dichloro-3-methyl-2-pentanone hydrochloride yielding a total of 132.1 g (90% overall yield) of 3-amino-1-chloro-3-methyl-1-pentanone hydrochloride.

l) Preparation of 4-amino-3-chloro-5-methoxyiminomethyl-N-(3-chloro-1-ethyl-1-methyl-2-oxopropyl)benzamide (Compound 2)

In a 5-liter three-necked round bottomed flask was placed 93 g of 3-amino-1-chloro-3-methyl-2-pentanone hydrochloride and 885 mL of water. To the resulting solution were added 138.6 g of sodium bicarbonate followed by 500 mL of ethyl acetate. To the resulting well-stirred mixture was added 123.5 g of 4-amino-3-chloro-5-methoxyiminomethylbenzoyl chloride dissolved in 1000 mL of ethyl acetate at room temperature over a period of 50 minutes. After the addition was complete the reaction mixture was stirred at room temperature for 1 hour. The two phases were separated and the organic layer was washed with water (2×500 mL), brine (1×500 mL), dried over anhydrous magnesium sulfate and the solvent eliminated in a rotary evaporator yielding the crude product as a brown oil. This oil was passed through a short silica gel column using methylene chloride as elution solvent. Evaporation of the solvent yielded 133.3 g of the expected 4-amino-3-chloro-5-methoxyiminomethyl-N-(3-chloro-1-ethyl-1-methyl-2-oxopropyl)benzamide as an off-white solid (mp 140–141° C.).

Compounds 4 and 30 in Table 1

Compound 30 was prepared by the following procedure.

3-Nitro-N-(3-chloro-1-ethyl-1-methyl-2-oxopropyl) benzamide was prepared by reaction of 3-nitrobenzoylchloride with VIII as in scheme A (above), then converted to 3-amino-N-(3-chloro-1-ethyl-1-methyl-2-oxopropyl)benzamide by catalytic hydrogenation using palladium as the catalyst.

In a 300 ml, 4-necked, round-bottomed flask fitted with a mechanical stirrer, a thermometer and addition funnel was suspended 3.5 g of 3-amino-N-(3-chloro-1-ethyl-1-methyl-2-oxopropyl)benzamide in 100 ml of dichloromethane. The mixture was cooled to 0–5° C. in an ice bath, then 1.8 ml of triethylamine was added and the mixture allowed to stir for a few minutes. Methylchloroformate (1.1 ml) was added slowly, dropwise keeping the temperature under 5° C., and the mixture stirred for 20 minutes. The ice bath was removed and the reaction mixture allowed to warm to room temperature. The reaction mixture was washed twice with 50 ml of water and dried over anhydrous magnesium sulfate. The solvent was removed using a rotary evaporator, yielding the crude product. The crude product was purified by chromatography on silica gel, yielding 230 mg of compound 30.

Compound 4 was prepared by the same procedure as compound 30, but using 4-nitrobenzoylchloride as the starting material.

Compounds in Tables 2, 3, 4 and 5

Compounds in Tables 2, 3, 4 and 5 were prepared according to synthetic methods described in U.S. Pat. No. 4,863,940.

Compounds 40, 41, 42, 43 and 44 in Table 6

Compounds 40, 41, 43 and 44 were prepared by reaction of the corresponding aromatic derivative (VII), in which $R^4$ and $R^5$ together form a fused ring, with 3-amino-1-chloro-3-methyl-2-pentanone hydrochloride (compound VIII in which $R^1$ is methyl and $R^2$ is ethyl) as illustrated above in Scheme A:

To prepare compound 42, 6-carboxy-1,3-benzothiazole (purchased from Maybridge Chemical Company Ltd.) was first treated with thionyl chloride to give the acid chloride. The acid chloride was treated with 3-amino-1-chloro-3-methyl-2-pentanone hydrochloride in the presence of triethylamine to yield compound 42.

To prepare the aromatic portion of compound 41, the 5-carboxy benzoxazole derivative XIV was prepared from the corresponding 2-amino phenol derivative by procedures known in the art and described in, for example, E. C. Taylor, ed., *The Chemistry of Heterocyclic Compounds*, vol. 47, John Wiley & Sons, 1987 "Synthesis of Fused Heterocycles", edited by G. P. Ellis; p. 50, part I and pp. 713–714 part II). This procedure is set forth below:

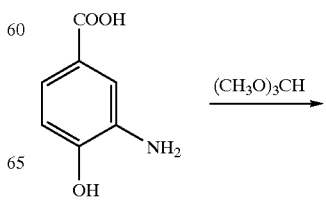

XIV

-continued

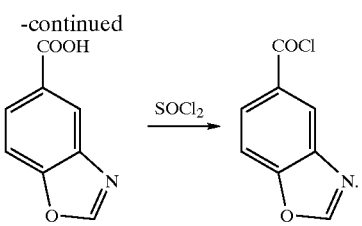

XIV was then treated with 3-amino-1-chloro-3-methyl-2-pentanone hydrochloride in the presence of triethylamine to yield compound 41.

To prepare the aromatic portions of compounds 40, 43 and 44, the 6-carboxy benzoxazole derivatives (XV) were prepared from the corresponding 2-amino phenol derivatives by the procedure set forth below:

XV

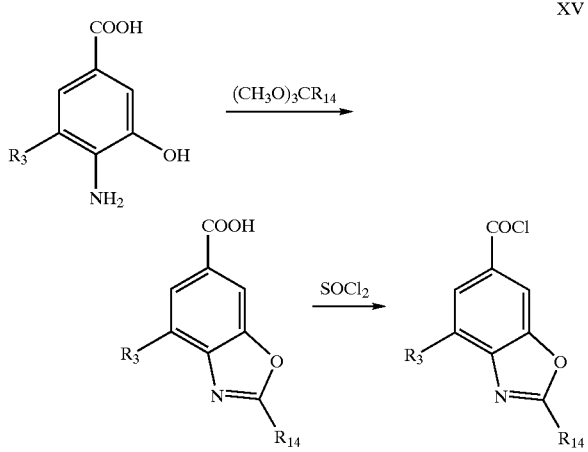

wherein $R^{14}$ is H or $CH_3$.

To prepare compound 40, 6-carboxy-1,3-benzoxazole was prepared from 4-amino-3-hydroxy benzoic acid by treatment with trimethylorthoformate. 6-Carboxy-1,3-benzoxazole was first treated with thionyl chloride to give the acid chloride. The acid chloride was treated with 3-amino-1-chloro-3-methyl-2-pentanone hydrochloride in the presence of triethylamine to yield compound 40.

To prepare compound 43, 6-carboxy-4-chloro-1,3-benzoxazole was prepared from 4-amino-5-chloro-3-hydroxy benzoic acid by treatment with trimethylorthoformate. 6–Carboxy-4-chloro-1,3-benzoxazole was first treated with thionyl chloride to give the acid chloride. The acid chloride was treated with 3-amino-1-chloro-3-methyl-2-pentanone hydrochloride in the presence of triethylamine to yield compound 43.

To prepare compound 44, 6-carboxy-2-methyl-4-chloro-1,3-benzoxazole was prepared from 4-amino-5-chloro-3-hydroxy benzoic acid by treatment with trimethylorthoacetate. 6–Carboxy-2-methyl-4-chloro-1,3-benzoxazole was first treated with thionyl chloride to give the acid chloride. The acid chloride was treated with 3-amino-1-chloro-3-methyl-2-pentanone hydrochloride in the presence of triethylamine to yield compound 44.

The following examples are provided in order to illustrate the method of the present invention.

EXAMPLE 1

The ability of compound 3 to bind covalently to beta-tubulin when applied to the Oomycete fungus *Phytophthora capsici* is shown in this example.

Figure 3:
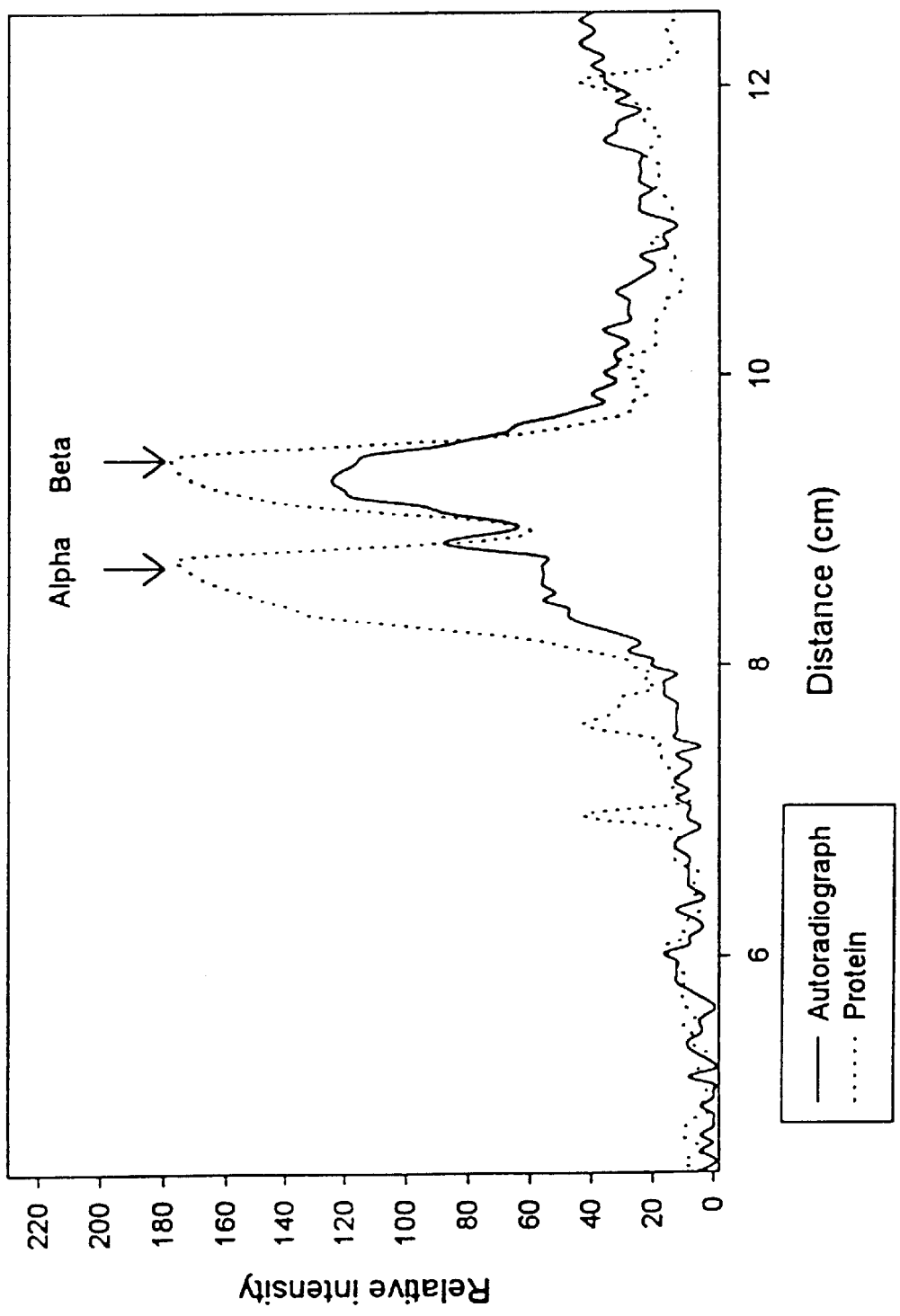
FIG. 3 depicts an analysis of radiolabeled protein by sodium dodecyl sulfate polyacrylamide gel electrophoresis and autoradiography following treatment of isolated bovine tubulin with $^{14}$C-labeled compound 1.

*P. capsici* (ATCC15399) was maintained on V-8 agar, pH 7.0, containing 200 ml V-8 juice, 4 g $CaCO_3$, and 20 g agar per liter. An erlenmeyer flask (125 ml capacity) containing 20 ml of the asparagine-sucrose medium described by Erwin, D. C. and Katznelson, K., 1971, Canadian Journal of Microbiology, vol. 7, p. 15–25 (1971) was inoculated with a mycelial plug (7 mm in diameter) cut from the growing edge of a culture of *P. capsici* grown on V-8 agar. The flask was incubated at 26° C. with shaking at 120 rpm on a gyrotary shaker for 72 hours, then 50 $\mu$l of 0.8 mM $^{14}$C-labeled compound 3 was added. After further incubation for 1 hour, the fungal mycelium was collected by filtration and washed with 100 ml of water. The mycelium was frozen in liquid nitrogen and ground to a fine powder. Proteins were extracted under denaturing conditions (heating for 5 minutes at 100° C. in 62 mM Tris-HCl buffer, pH 6.8, containing 3% sodium dodecyl sulfate, 5% mercaptoethanol and 10% glycerol) expected to cause dissociation of any noncovalently-bound ligand. Aliquots of the extracted proteins were subjected to sodium dodecyl sulfate polyacrylamide gel electrophoresis (SDS-PAGE) to separate the proteins according to Laemmli, U. K., Nature (London), vol. 277, pp. 680–685, 1970 on duplicate 7.5% polyacrylamide gels. One gel was stained for protein with Coomassie brilliant blue R250. Proteins from the second gel were transferred electrophoretically to a nitrocellulose membrane. The membrane was sprayed with EN$^3$HANCE™ spray (Dupont NEN Research Products) and the location of radio-labeled protein was determined by autoradiography using Kodak X-OMAT AR film with a 3 week exposure. The location of beta-tubulin on the nitrocellulose was determined by immunolabeling with a monoclonal antibody against beta-tubulin. Results are presented in FIG. 1. The dashed line represents a densitometric scan of the Coomassie stained gel and shows the distribution of proteins. The solid line represents a densitometric scan of the autoradiograph, and shows a single $^{14}$C-labeled band. The location of beta-tubulin as determined by immunolabeling is indicated by an arrow and coincided with the position of the $^{14}$C-labeled protein band.

EXAMPLE 2

The ability of compound 1 to bind covalently to beta-tubulin when applied to suspension-cultured tobacco cells is shown in this example.

Suspension-cultured tobacco cells were grown at 27° C. on a gyrotary shaker at 200 rpm in growth medium prepared according to Nagata, K. et al., Molecular and General Genetics, vol. 184, pp. 161–165 (1981). Cells were treated with $^{14}$C-labeled compound 1 at a concentration of 10 $\mu$M for 1 hour, then collected by filtration. The cells were frozen in liquid nitrogen and ground to a fine powder, then the proteins were extracted and separated on duplicate gels by SDS-PAGE as described in Example 1. One gel was stained for protein and the second gel analyzed by autoradiography and immunolabeling as described in Example 1. Results are presented in FIG. 2. The dashed line represents a densitometric scan of the Coomassie stained gel and shows the distribution of proteins. The solid line represents a densitometric scan of the autoradiograph, and shows a single $^{14}$C-labeled band. The location of beta-tubulin as determined by immunolabeling is indicated by an arrow and coincided with the position of the $^{14}$C-labeled protein band.

EXAMPLE 3

The ability of compound 1 to bind covalently to the beta-subunit of isolated bovine tubulin is shown in this example.

Tubulin was isolated from bovine brain using the method described by Vallee, R. B. in Methods in Enzymology vol. 134, pp. 89–104 (1986). Tubulin (10 μM) in 1.0 M sodium glutamate, pH 6.6 containing 1 mM $MgCl_2$ was incubated with 25 μM $^{14}C$-labeled compound 1 for 4 hours at 37° C. The sample was transferred to an ice bath for 3 minutes, and the tubulin was precipitated by addition of 20% trichloroacetic acid and incubation on ice for a further 20 minutes. After centrifugation at 12,000 g for 5 minutes the tubulin pellet was washed once with 80% ice-cold acetone, and dissolved in 62 mM Tris-HCl buffer, pH 6.8, containing 3% sodium dodecyl sulfate, 5% mercaptoethanol and 10% glycerol at room temperature. The sample was heated for 2 minutes at 100° C., then aliquots were subjected to SDS-PAGE on duplicate gels as described in Example 1. One gel was stained for protein and the second gel analyzed by autoradiography and immunolabeling as described in Example 1. Immunolabeling was carried out using monoclonal antibodies against both beta-tubulin and alpha-tubulin. Results are presented in FIG. 3. The positions of alpha-tubulin and beta-tubulin as determined by immunolabelling are indicated by arrows. The dashed line represents a densitometric scan of the Coomassie stained gel and shows the distribution of proteins, with two main protein bands corresponding to alpha-tubulin and beta-tubulin. The solid line represents a densitometric scan of the autoradiograph, and shows predominant labeling of the beta-tubulin subunit.

EXAMPLE 4

The effects of various antitubulin compounds from different chemical classes on binding of compound 1 to tubulin in tobacco suspension-cultured cells is shown in this example.

Aliquots (2 ml) of suspension-cultured tobacco cells grown as described in Example 2 were added to 25 ml capacity glass vials. Each vial then received 5 μl of DMSO (control) or 5 μl of an antitubulin compound dissolved in DMSO. Vials were incubated with shaking at 27° C. for 2 hours, then 5 μl of a 100 μM solution of tritium-labeled compound 1 in DMSO was added. Vials were incubated with shaking at 27° C. for 20 minutes, then binding of the radioligand was stopped by adding 5 μl of unlabeled 40 mM compound 1. The samples were incubated with shaking at 27° C. for a further 20 minutes, then transferred to 15 ml capacity polypropylene centrifuge tubes in an ice bath. Each vial was rinsed with 2 ml ice-cold growth medium (described in example 2) and the rinse solution was then added to the rest of the sample. Following centrifugation at 4° C. for 3 minutes at 2,500 rpm the supernatant was discarded and the pelleted cells were resuspended in 4 ml of ice-cold 10% trichloroacetic acid. Samples were kept for 1 hour in an ice bath, centrifuged again, and the cells resuspended in 4 ml of ice-cold ethanol. After incubation for a further 1 hour in an ice-bath the cells were collected by filtration on glass fiber filters and washed twice with 10 ml of ice-cold ethanol. The filters with washed cells were transferred to scintillation vials, 10 ml of Hydrofluor™ scintillation fluid (National Diagnostics, Manville, N.J.) was added to each, and the samples were counted in a scintillation counter to determine the amount of bound radioactivity. The effects of different antitubulin compounds on binding of the radioligand are presented in Table 7 with the amounts of radioligand bound in the presence of each antitubulin compound expressed as a percentage of the amount of radioligand bound in the DMSO control. Paclitaxel and the antitubulin herbicides pronamide and chlorpropham reduced binding of the radioligand, while the antitubulin herbicide trifluralin increased binding of the radioligand.

TABLE 7

Effect of various antitubulin compounds on binding of tritiated compound 1 to tubulin in a whole cell binding assay using tobacco suspension-cultured cells.

| Antitubulin compound | Concentration (μM) | Binding of radioligand (% control) |
|---|---|---|
| None (DMSO control) | | 100.0 |
| Paclitaxel | 25 | 50.3 |
| Pronamide | 100 | 68.7 |
| Trifluralin | 100 | 129.0 |
| Chlorpropham | 100 | 29.1 |

EXAMPLE 5

The effect of paclitaxel on binding of compound 1 to tubulin in *Phytophthora capsici* is shown in this example.

A liquid mycelial shake culture of *P. capsici* in asparagine-sucrose medium was used to prepare a homogeneous suspension of fungal material for binding assays. Asparagine-sucrose medium (100 ml) was inoculated with mycelial plugs cut from cultures grown on V-8 agar, and incubated at 26° C. on a gyrotary shaker for 48 hours. The culture was homogenized in a blender, and 30 ml of the homogenate subcultured into 100 ml of fresh medium, which was then incubated at 26° C. on a gyrotary shaker for 17 hours. The resulting mycelium was recovered from the medium by centrifugation and resuspended in 1170 ml of fresh medium. Aliquots (2 ml) of this suspension were added to 25 ml capacity glass vials. Each vial then received 5 μl of DMSO (control) or 5 μl of paclitaxel dissolved in DMSO. Vials were incubated with shaking at 26° C. for 1 hour, then 5 μl of a 100 μM solution of tritium-labeled compound 1 in DMSO was added. Vials were incubated with shaking at 26° C. for 20 min, then binding of the radioligand was stopped by adding 5 μl of unlabeled 40 mM compound 1. The samples were incubated with shaking at 27° C. for a further 20 minutes, then transferred to 15 ml capacity centrifuge tubes in an ice bath. Each vial was rinsed with 2 ml ice-cold medium which was then added to the rest of the sample. Following centrifugation at 4° C. for 5 minutes at 3,400 rpm, the supernatant was discarded and the pelleted cells were resuspended in 4 ml of ice-cold 10% trichloroacetic acid. Samples were kept for 1 hour in an ice bath, centrifuged again, and the cells resuspended in 4 ml of ice-cold ethanol. After incubation for a further 2 hours in an ice-bath the cells were collected by filtration on glass fiber filters and washed twice with 10 ml of ice-cold ethanol. The filters with washed cells were transferred to scintillation vials, 10 ml of Hydrofluor™ scintillation fluid was added, and the samples were counted in a scintillation counter to determine the amount of bound radioactivity. The effect of paclitaxel at various concentrations on binding of the radioligand are presented in Table 8, with the amounts of radioligand bound in the presence of paclitaxel expressed as a percentage of the amount of radioligand bound in the DMSO control.

TABLE 8

Effect of paclitaxel on binding of tritiated compound 1 to tubulin in a whole cell binding assay using *Phytophthora capsici* mycelium*

| Treatment | Concentration ($\mu$M) | Binding of radioligand (% control) |
|---|---|---|
| None (DMSO control) | | 100.0 |
| Paclitaxel | 0.004 | 84.5 |
| Paclitaxel | 0.02 | 54.6 |
| Paclitaxel | 0.1 | 34.6 |
| Paclitaxel | 0.5 | 23.6 |

EXAMPLE 6

The effect of zarilamide and compounds 7, 8, 16, 19, 23 and 27 described in Table 1 on binding of compound 1 to tubulin in *Phytophthora capsici* is shown in this example.

Zoospores of *P. capsici* were prepared as follows. Petri plates, 9 cm in diameter, containing 15 ml of V-8 agar were inoculated with a mycelial plug of *P. capsici* and incubated for 4 days in the dark at 25° C., then placed under continuous fluorescent light for 3 days to induce sporulation. To induce zoospore release, 15 ml of sterile water was added to each plate. The plates were incubated at room temperature for 10 minutes, followed by 20 minutes at 4° C., and finally returned to room temperature for 15 minutes. The zoospore-containing fluid was then removed from each plate and adjusted to a density of $5\times10^5$ zoospores per ml. Assay tubes containing germinated zoospores cysts were prepared by adding 100 $\mu$l of zoospore suspension to 400 $\mu$l of asparagine-sucrose medium in 16×1.25 cm polypropylene tubes, which were then loosely capped and incubated on a gyrotary shaker at 120 rpm for 24 hours at 26° C.

Tubes containing germinated zoospore cysts then received 2.5 $\mu$l of DMSO (control) or 2.5 $\mu$l of test compound dissolved in DMSO. Each compound was tested at a series of concentrations. Tubes were incubated with shaking at 26° C. for 1 hour, then 2.5 $\mu$l of a 40 $\mu$M solution of tritium-labeled compound 1 in DMSO were added. Vials were incubated with shaking at 26° C. for 20 minutes, then binding of the radioligand was stopped by adding 1.5 ml of ice-cold unlabeled 133 $\mu$M compound 1, and transferring the tubes to an ice bath. Following centrifugation at 3,400 rpm for 3 minutes, the supernatant was discarded and the pelleted cells were resuspended in 2 ml of ice-cold 10% trichloroacetic acid. Samples were kept for 1 hour in an ice bath, centrifuged again, and the cells resuspended in 2 ml of ice-cold ethanol. After incubation for a further 1 hour in an ice-bath, an additional 4 ml of ice-cold ethanol was added to each tube and the cells were collected by filtration on glass fiber filters in a Brandell cell harvester (Brandel Biomedical Research and Development Laboratories, Inc., Gaithersburg, Md.), and washed twice with 4 ml of ice-cold ethanol. The filters with washed cells were transferred to scintillation vials and 0.1 ml of water was added followed by 1 ml of Protosol™ (Dupont NEN Research Products). The vials were incubated at 60° C. for 30 minutes and cooled to room temperature. Ten ml of Econofluor™ scintillation fluid (Dupont NEN Research Products) was added, and the samples were counted in a scintillation counter to determine the amount of bound radioactivity. IC50 values for each test compound (defined as the concentration required to inhibit binding of the radioligand by 50% as compared to controls lacking the test compound) were determined from dose-response curves and are presented in Table 9.

TABLE 9

| Compound | IC50 ($\mu$g/ml) |
|---|---|
| Zarilamide | 7.02 |
| 7 | 0.98 |
| 8 | 0.25 |
| 16 | 1.17 |
| 19 | 0.25 |
| 23 | 0.06 |
| 27 | 1.83 |

EXAMPLE 7

The utility of compound 1 as a probe to detect effects of antitubulin compounds on isolated bovine tubulin is shown by this example.

Assay mixtures contained 10 $\mu$M isolated tubulin in 1.0 M sodium glutamate, pH 6.6 containing 1 mM $MgCl_2$, and 2.5 $\mu$DMSO (control) or 2.5 $\mu$l of test compound dissolved in DMSO in 0.5 ml polypropylene tubes. Mixtures were incubated at 37° C. for 30 minutes, then 2.5 $\mu$l of a 640 $\mu$M solution of tritium-labeled compound 1 in DMSO was added. After further incubation at 37° C. for 120 minutes, aliquots (80 $\mu$l) of the assay mixtures were applied to 2.3 cm diameter Whatman 3MM filter paper disks, which were dried for 15 seconds under warm air, immersed in 3 ml of ice-cold 10% trichloroacetic acid, and left overnight at 4° C. Disks were transferred to 5% trichloroacetic acid for 30 minutes, washed twice more in 5% trichloroacetic acid, washed for 30 minutes at 37° C. in ethanol/ether (1:1, v/v), then for 15 min at room temperature in ethanol/ether (1:1, v/v), and finally in two successive washes for 15 minutes each in ether at room temperature. The disks were dried, transferred to scintillation vials containing 10 ml of Hydrofluor™ and counted in a scintillation counter. The effects of antitubulin compounds at 100 $\mu$M final concentration on binding of the radioligand are presented in Table 10 with the amount of radioligand bound in the presence of each antitubulin compound expressed as a percentage of the amount of radioligand bound in the DMSO control.

TABLE 10

| Compound | Binding (% control) |
|---|---|
| Colchicine | 18.7 |
| Podophyllotoxin | 21.7 |
| Nocodazole | 31.3 |
| Vinblastine | 90.7 |

EXAMPLE 8

Effect of antitubulin compounds on binding of the tritiated S-enantiomer of compound 2 to tubulin in a whole cell binding assay using the colon cancer cell line HCT-116 is shown by this example.

The colon cancer cell line HCT-116 (obtained from the American Type Culture Collection) was cultured in 75 $cm^2$ flasks containing McCoy's 5a Modified Medium with 10% heat-inactivated fetal bovine serum, 50 U/ml of penicillin G and 50 U/ml of streptomycin sulfate. A cell suspension was prepared by trypsinization of the culture, and adjusted to a density of $10^6$ cells/ml by dilution into incomplete medium (medium lacking serum, penicillin G and streptomycin). Aliquots (150 $\mu$l) of cell suspension were added to wells of 96-well glass fiber filter plates (Millipore Multiscreen® plates, 1 μm glass fiber, Type B). Wells then received 30 μl of a solution of the test antitubulin compound in incomplete medium/DMSO mixture (8.5:1, v/v) or 30 μl of the incomplete medium/DMSO mixture alone (control). After mixing, the plates were incubated at 37° C. for 1 hour, then 25 μl of 0.8 μM tritium-labeled S-enantiomer of compound 2 was added to each well. After mixing, the plates were incubated at 37° C. for 1 hour, then binding of the radioligand to tubulin was stopped by adding 50 μl of 100 μM unlabeled compound 2. The fluid was removed from the plate by vacuum filtration through the glass fiber, then 100 μl of ice-cold 10% trichloroacetic acid was added to each well. The plates were incubated for 1 h at 4° C., then the fluid was removed by filtration. Ice-cold ethanol (250 μl) was added to each well, the plates incubated for 1 h at 4° C., then the ethanol was removed by filtration. Wells were washed 4 more times with 250 μl of ice-cold ethanol. After drying the plates at 37° C. for 20 min, the glass fiber filters were punched out of the wells into scintillation vials, 5 ml of scintillation fluid was added to each vial, and the samples were counted in a scintillation counter to determine the amount of bound radioactivity. The effects of different antitubulin compounds on binding of the radioligand are presented in Table 11 with the amounts of radioligand bound in the presence of each antitubulin compound expressed as a percentage of the amount of radioligand bound in the control. Paclitaxel, colchicine, podophyllotoxin and nocodazole reduced binding of the radioligand, while vinblastine increased binding of the radioligand, presumably by increasing affinity of tubulin for the radioligand through an allosteric interaction.

TABLE 11

| Antitubulin compound | Binding of radioligand (% control) | | | |
| --- | --- | --- | --- | --- |
| | 0.1 μM | 1 μM | 10 μM | 100 μM |
| Paclitaxel | 37 | 19 | 6 | 4 |
| Podophyllotoxin | 37 | 0 | 0 | 0 |
| Colchicine | 105 | 79 | 0 | 0 |
| Nocodazole | 102 | 99 | 74 | 44 |
| Vinblastine | 155 | 218 | 286 | 323 |

It should be understood that the instant specification is set forth by way of illustration and not limitation, and that various modifications and changes can be made without departing from the spirit and scope of the present invention as defined by the appended claims.

I claim:

1. A method for carrying out binding assays, which are useful for screening test compounds for antitubulin activity, comprising (i) incubating eukaryotic cells, cell extracts or isolated tubulin with an amide probe in the absence of a test compound, (ii) determining a rate of binding of the amide probe to tubulin in the eukaryotic cells, cell extracts or isolated tubulin in the absence of a test compound, (iii) if the rate of binding of the amide probe to tubulin in the eukaryotic cells, cell extracts or isolated tubulin in the absence of a test compound is greater than zero, incubating the eukaryotic cells, cell extracts or isolated tubulin with the test compound, (iv) adding the amide probe to the eukaryotic cells, cell extracts or isolated tubulin either simultaneously with the addition of the test compound or subsequent to the addition of the test compound, measuring the rate of binding of the amide probe to tubulin in the eukaryotic cells, cell extracts or isolated tubulin, and (v) determining the antitubulin activity of the test compound as indicated by a reduction or enhancement of the rate of binding of the amide probe to tubulin in the eukaryotic cells, cell extracts or isolated tubulin containing the test compound relative to the rate of binding of the amide probe to tubulin in the eukaryotic cells, cell extracts or isolated tubulin in the absence of the test compound; the amide probe capable of binding covalently to tubulin and inhibiting the growth of eukaryotic cells, the amimde probe having the structural formula:

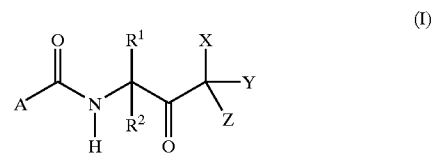

(I)

wherein

A is phenyl, pyridyl, furyl, thienyl, isoxazolyl, oxazolyl, pyrrolyl, isothiazolyl, thiazolyl, pyrazolyl, imidazolyl or ($C_3$–$C_7$)cycloalkyl; which are optionally, substituted with up to three substituents each independently selected from halo, cyano, ($C_1$–$C_4$)alkyl, halo($C_1$–$C_4$)alkyl, ($C_2$–$C_4$)alkenyl, halo($C_2$–$C_4$)alkenyl, ($C_2$–$C_4$)alkynyl, halo($C_2$–$C_4$)alkynyl, ($C_1$–$C_4$)alkoxy, halo($C_1$–$C_4$)alkoxy, ($C_1$–$C_4$)alkylthio, halo($C_1$–$C_4$)alkylthio, nitro, —$NR^6R^7$, —$CR^8$=$NOR^9$, —$NHCOOR^{10}$, —$CONR^{11}R^{12}$, and —$COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, ($C_1$–$C_4$)alkyl, halo($C_1$–$C_4$)alkyl, ($C_2$–$C_4$)alkenyl, halo($C_2$–$C_4$)alkenyl, ($C_2$–$C_4$)alkynyl or halo($C_2$–$C_4$)alkynyl, provided that both $R^1$ and $R^2$ are not a hydrogen atom;

$R^6$ and $R^7$ are each independently a hydrogen atom, ($C_1$–$C_4$)alkyl or ($C_1$–$C_4$)alkylcarbonyl;

$R^8$ is a hydrogen atom, ($C_1$–$C_4$)alkyl, ($C_2$–$C_4$)alkenyl or ($C_2$–$C_4$)alkynyl;

$R^9$ is a hydrogen atom, ($C_1$–$C_4$)alkyl, ($C_2$–$C_4$)alkenyl, ($C_2$–$C_4$)alkynyl or ($C_1$–$C_4$)alkylcarbonyl;

$R^{10}$, $R^{11}$, $R^{12}$ and $R^{13}$ are each independently a hydrogen atom, ($C_1$–$C_4$)alkyl, ($C_2$–$C_4$)alkenyl or ($C_2$–$C_4$)alkynyl; and X, Y and Z are each independently a hydrogen atom, halo, cyano, thiocyano or isothiocyano, provided that at least one of X, Y and Z is not a hydrogen atom; or the optical enantiomers thereof.

2. A method for evaluating the sensitivity of a test cell population to an antitubulin compound comprising (i) incubating cells, cell extracts or isolated tubulin of the test cell population with an amide probe in the absence of an antitubulin test compound, (ii) determining a rate of binding of the amide probe to tubulin in the eukaryotic cells, cell extracts or isolated tubulin in the absence of the antitubulin test compound, (iii) if the rate of binding of the amide probe to tubulin in the eukaryotic cells, cell extracts or isolated tubulin in the absence of the antitubulin test compound is greater than zero, incubating the eukaryotic cells, cell extracts or isolated tubulin of the test cell population with the antitubulin compound, (iv) adding the amide probe to the cells, cell extracts or isolated tubulin of the test cell population either simultaneously with the addition of the antitubulin compound or subsequent to the addition of the antitubulin compound and measuring the rate of binding of the amide probe to tubulin in the cells, cell extracts or isolated tubulin of the test cell population, and (v) determining the sensitivity of the test cell population to the antitubulin compound by comparing the ability of the antitubulin compound to affect binding of the amide probe in the cells, cell extracts or isolated tubulin of the test cell population with its ability to affect binding of the amide probe in cells, cell extracts or isolated tubulin from cell populations of known sensitivity to the antitubulin compound, the amide probe capable of binding covalently to tubulin and inhibiting the growth of eukaryotic cells, the amide probe having the structural formula:

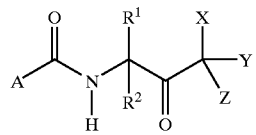

(I)

wherein

A is phenyl, pyridyl, furyl, thienyl, isoxazolyl, oxazolyl, pyrrolyl, isothiazolyl, thiazolyl, pyrazolyl, imidazolyl, ($C_3$–$C_7$)cycloalkyl, pyrimidinyl, quinolyl, isoquinolyl, naphthyl, pyridazinyl, pyrazinyl, benzothienyl, indolyl, benzofuranyl or benzyl; which are optionally, substituted with up to three substituents each independently selected from halo, cyano, ($C_1$–$C_4$)alkyl, halo($C_1$–$C_4$) alkyl, ($C_2$–$C_4$)alkenyl, halo($C_2$–$C_4$)alkenyl, ($C_2$–$C_4$) alkynyl, halo($C_2$–$C_4$)alkynyl, ($C_1$–$C_4$)alkoxy, halo ($C_1$–$C_4$)alkoxy, ($C_1$–$C_4$)alkylthio, halo($C_1$–$C_4$) alkylthio, nitro, —$NR^6R^7$, —$CR^8$=$NOR^9$, —$NHCOOR^{10}$, —$CONR^{11}R^{12}$, and —$COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, ($C_1$–$C_4$)alkyl, halo($C_1$–$C_4$)alkyl, ($C_2$–$C_4$)alkenyl, halo ($C_2$–$C_4$)alkenyl, ($C_2$–$C_4$)alkynyl or halo($C_2$–$C_4$) alkynyl, provided that both $R^1$ and $R^2$ are not a hydrogen atom;

$R^6$ and $R^7$ are each independently a hydrogen atom, ($C_1$–$C_4$)alkyl or ($C_1$–$C_4$)alkylcarbonyl;

$R^8$ is a hydrogen atom, ($C_1$–$C_4$)alkyl, ($C_2$–$C_4$)alkenyl or ($C_2$–$C_4$)alkynyl;

$R^9$ is a hydrogen atom, ($C_1$–$C_4$)alkyl, ($C_2$–$C_4$)alkenyl, ($C_2$–$C_4$)alkynyl or ($C_1$–$C_4$)alkylcarbonyl;

$R^{10}$, $R^{11}$, $R^{12}$ and $R^{13}$ are each independently a hydrogen atom, ($C_1$–$C_4$)alkyl, ($C_2$–$C_4$)alkenyl or ($C_2$–$C_4$) alkynyl; and X, Y and Z are each independently a hydrogen atom, halo, cyano, thiocyano or isothiocyano, provided that at least one of X, Y and Z is not a hydrogen atom; or the optical enantiomers thereof.

3. A method for carrying out binding assays, which are useful for resistance monitoring for antitubulin drugs or pesticides, comprising (i) measuring the rate of binding of an amide probe to tubulin in a test sample of eukaryotic cells, cell extracts or isolated tubulin from a cell population of unknown sensitivity to the antitubulin drug or pesticide and (ii) determining resistance as indicated by a reduction or enhancement of the rate of binding of the amide probe to tubulin in the test sample relative to the rate of binding of the amide probe to tubulin in a corresponding control sample of known sensitivity to the antitubulin drug or pesticide, the corresponding control sample having a previously determined rate of binding greater than zero for tubulin to the amide probe; the amide probe capable of binding covalently to tubulin and inhibiting the growth of eukaryotic cells, the amide probe having the structural formula:

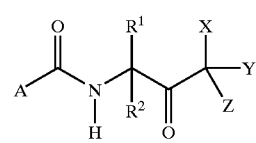

(I)

wherein

A is phenyl, pyridyl, furyl, thienyl, isoxazolyl, oxazolyl, pyrrolyl, isothiazolyl, thiazolyl, pyrazolyl, imidazolyl or ($C_3$–$C_7$)cycloalkyl; which are optionally, substituted with up to three substituents each independently selected from halo, cyano, ($C_1$–$C_4$)alkyl, halo($C_1$–$C_4$) alkyl, ($C_2$–$C_4$)alkenyl, halo($C_2$–$C_4$)alkenyl, ($C_2$–$C_4$) alkynyl, halo($C_2$–$C_4$)alkynyl, ($C_1$–$C_4$)alkoxy, halo ($C_1$–$C_4$)alkoxy, ($C_1$–$C_4$)alkylthio, halo($C_1$–$C_4$) alkylthio, nitro, —$NR^6R^7$, —$CR^8$=$NOR^9$, —$NHCOOR^{10}$, —$CONR^{11}R^{12}$, and —$COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, ($C_1$–$C_4$)alkyl, halo($C_1$–$C_4$)alkyl, ($C_2$–$C_4$)alkenyl, halo ($C_2$–$C_4$)alkenyl, ($C_2$–$C_4$)alkynyl or halo($C_2$–$C_4$) alkynyl, provided that both $R^1$ and $R^2$ are not a hydrogen atom;

$R^6$ and $R^7$ are each independently a hydrogen atom, ($C_1$–$C_4$)alkyl or ($C_1$–$C_4$)alkylcarbonyl;

$R^8$ is a hydrogen atom, ($C_1$–$C_4$)alkyl, ($C_2$–$C_4$)alkenyl or ($C_2$–$C_4$)alkynyl;

$R^9$ is a hydrogen atom, ($C_1$–$C_4$)alkyl, ($C_2$–$C_4$)alkenyl, ($C_2$–$C_4$)alkynyl or ($C_1$–$C_4$)alkylcarbonyl;

$R^{10}$, $R^{11}$, $R^{12}$ and $R^{13}$ are each independently a hydrogen atom, ($C_1$–$C_4$)alkyl, ($C_2$–$C_4$)alkenyl or ($C_2$–$C_4$) alkynyl; and X, Y and Z are each independently a hydrogen atom, halo, cyano, thiocyano or isothiocyano, provided that at least one of X, Y and Z is not a hydrogen atom; or the optical enantiomers thereof.

4. A method for carrying out binding assays, which are useful for determination of tubulin content in eukaryotic cells, cell extracts or isolated tubulin, comprising (i) incubating the cells, cell extracts or isolated tubulin preparations of unknown tubulin content with an amide probe and (ii) if the cells, cell extracts or isolated tubulin preparations of unknown tubulin content exhibit a binding rate of greater than zero, comparing the rate of binding or maximum extent of binding of the amide probe to tubulin in the sample of said unknown tubulin content with the rate of binding or maximum extent of binding of the amide probe to tubulin in a sample of known tubulin content; the amide probe capable of binding covalently to tubulin and inhibiting the growth of eukaryotic cells, the amide probe having the structural formula:

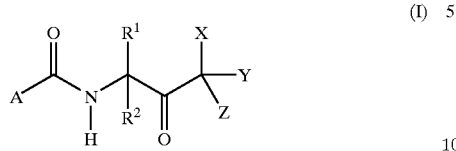

(I)

wherein

A is phenyl, pyridyl, furyl, thienyl, isoxazolyl, oxazolyl, pyrrolyl, isothiazolyl, thiazolyl, pyrazolyl, imidazolyl or $(C_3–C_7)$cycloalkyl; which are optionally, substituted with up to three substituents each independently selected from halo, cyano, $(C_1–C_4)$alkyl, halo$(C_1–C_4)$alkyl, $(C_2–C_4)$alkenyl, halo$(C_2–C_4)$alkenyl, $(C_2–C_4)$alkynyl, halo$(C_2–C_4)$alkynyl, $(C_1–C_4)$alkoxy, halo$(C_1–C_4)$alkoxy, $(C_1–C_4)$alkylthio, halo$(C_1–C_4)$alkylthio, nitro, $—NR^6R^7$, $—CR^8=NOR^9$, $—NHCOOR^{10}$, $—CONR^{11}R^{12}$, and $—COOR^{13}$; or when A is an unsaturated ring and is substituted with two or more substituents which are adjacent to one another, two of said substituents may form a fused 5, 6 or 7 membered ring containing up to two heteroatoms selected from oxygen, nitrogen, sulfur and phosphorous;

$R^1$ and $R^2$ are each independently a hydrogen atom, $(C_1–C_4)$alkyl, halo$(C_1–C_4)$alkyl, $(C_2–C_4)$alkenyl, halo$(C_2–C_4)$alkenyl, $(C_2–C_4)$alkynyl or halo$(C_2–C_4)$alkynyl, provided that both $R^1$ and $R^2$ are not a hydrogen atom;

$R^6$ and $R^7$ are each independently a hydrogen atom, $(C_1–C_4)$alkyl or $(C_1–C_4)$alkylcarbonyl;

$R^8$ is a hydrogen atom, $(C_1–C_4)$alkyl, $(C_2–C_4)$alkenyl or $(C_2–C_4)$alkynyl;

$R^9$ is a hydrogen atom, $(C_1–C_4)$alkyl, $(C_2–C_4)$alkenyl, $(C_2–C_4)$alkynyl or $(C_1–C_4)$alkylcarbonyl;

$R^{10}$, $R^{11}$, $R^{12}$ and $R^{13}$ are each independently a hydrogen atom, $(C_1–C_4)$alkyl, $(C_2–C_4)$alkenyl or $(C_2–C_4)$alkynyl; and X, Y and Z are each independently a hydrogen atom, halo, cyano, thiocyano or isothiocyano, provided that at least one of X, Y and Z is not a hydrogen atom; or the optical enantiomers thereof.

5. The method of claim 1, 2, 3 or 4 using amides having the structural formula

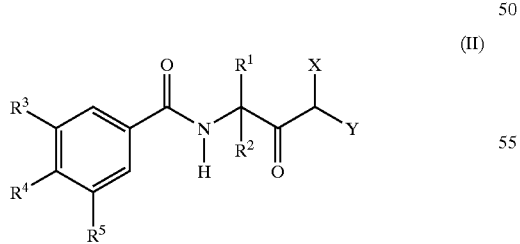

(II)

wherein $R^1$ and $R^2$ are each independently a hydrogen atom, $(C_1–C_4)$alkyl, halo$(C_1–C_4)$alkyl, $(C_2–C_4)$alkenyl or $(C_2–C_4)$alkynyl, provided that both $R^1$ and $R^2$ are not a hydrogen atom;

$R^3$, $R^4$, and $R^5$ are each independently a hydrogen atom, halo, cyano, $(C_1–C_4)$alkyl, halo$(C_1–C_4)$alkyl, $(C_2–C_4)$alkenyl, $(C_2–C_4)$alkynyl, $(C_1–C_4)$alkoxy, $(C_1–C_4)$alkylthio, halo$(C_1–C_4)$alkoxy, nitro, $—NR^6R^7$, $—CR^8=NOR^9$, $—NHCOOR^{10}$, $—CONR^{11}R^{12}$ or $—COOR^3$; or $R^4$ and $R^5$ taken together form a fused 5, 6, or 7 membered ring, which may contain up to two heteroatoms selected from the group consisting of O, S, N and P;

$R^6$, $R^7$, $R^8$, $R^9$, $R^{10}$, $R^{11}$, $R^{12}$, and $R^{13}$ are each independently a hydrogen atom or $(C_1–C_4)$alkyl; and X and Y are each independently a hydrogen atom, halo, cyano, thiocyano or isothiocyano, provided that both X and Y are not a hydrogen atom; or the optical enantiomers thereof.

6. The method of claim 5 using benzoic acid amides having the structural formula (II) wherein $R^1$ is methyl;

$R^2$ is methyl or ethyl;

$R^3$ and $R^5$ are each independently a hydrogen atom, halo, methyl, nitro, cyano, $—NR^6R^7$, $—CR^8=NOR^9$ or $—NHCOOR^{10}$, provided that both $R^3$ and $R^5$ are not a hydrogen atom;

$R^4$ is a hydrogen atom, halo, $—NR^6R^7$, cyano, $—CR^8=NOR^9$, $—NHCOOR^{10}$, $—COOR^{13}$, or $(C_1–C_4)$alkyl;

$R^6$, $R^7$, $R^8$, $R^9$, $R^{10}$ and $R^{13}$ are each independently a hydrogen atom or $(C_1–C_4)$alkyl;

X is chloro; and

Y is a hydrogen atom; or the optical enantiomers thereof.

7. In assays employing mammalian cells, cell extracts or tubulin, the method of claim 6 using benzoic acid amides having the structural formula (II) wherein $R^1$ is methyl, $R^2$ is ethyl, $R^3$ is halo or cyano, $R^4$ and $R^5$ are amino or $—CH=NOCH_3$ provided that $R^4$ and $R^5$ are not the same, X is chloro, and Y is a hydrogen atom; or the optical enantiomers thereof.

8. In assays employing fungal cells, cell extracts or tubulin in which the fungus belongs to the Ascomycete, Deuteromycete or Basidiomycete classes of fungi, the method of claim 6 using benzoic acid amides having the structural formula (II) wherein $R^1$ is methyl, $R^2$ is methyl or ethyl, $R^3$ is $—CH=NOCH_3$, $R^4$ is a hydrogen atom, halo, amino, cyano or methyl, $R^5$ is halo, methyl, nitro or cyano, X is chloro and Y is a hydrogen atom; or the optical enantiomers thereof.

9. In assays employing fungal cells, cell extracts or tubulin in which the fungus belongs to the Oomycete class of fungi, the method of claim 6 using benzoic acid amides having the structural formula (II) wherein $R^1$ is methyl, $R^2$ is ethyl, $R^3$ and $R^5$ are each independently a hydrogen atom, halo, methyl, nitro, cyano, $—NR^6R^7$, $—CR^8=NOR^9$ or $—NHCOOR^{10}$, provided that both $R^3$ and $R^5$ are not a hydrogen atom, R⁴ is a hydrogen atom, halo, —NR⁶R⁷, cyano, —CR⁸=NOR⁹, —NHCOOR¹⁰, —COOR¹³ or (C₁–C₄)alkyl, R⁶, R⁷, R⁸, R⁹, R¹⁰ and R¹³ are each independently a hydrogen atom or methyl, X is chloro, and Y is a hydrogen atom; or the optical enantiomers thereof.

10. In assays employing plant cells, cell extracts or tubulin, the method of claim 6 using benzoic acid amides having the structural formula (II) wherein R¹ is methyl, R² is methyl or ethyl, R³ and R⁵ are each independently a hydrogen atom, halo, methyl, nitro or cyano, provided that both R³ and R⁵ are not a hydrogen atom, R⁴ is a hydrogen atom, X is chloro, and Y is a hydrogen atom; or the optical enantiomers thereof.

11. The method of claim 1, 2, 3 or 4 using pyridinecarboxamides having the structural formula

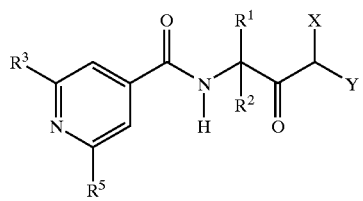

(III)

wherein

R¹ and R² are each independently a hydrogen atom, (C₁–C₄)alkyl, halo(C₁–C₄)alkyl, (C₂–C₄)alkenyl or (C₂–C₄)alkynyl, provided that both R¹ and R² are not a hydrogen atom;

R³ and R⁵ are each independently a hydrogen atom, halo, cyano, (C₁–C₄)alkyl, halo(C₁–C₄)alkyl, (C₂–C₄) alkenyl, (C₂–C₄)alkynyl, (C₁–C₄)alkoxy, (C₁–C₄) alkylthio, halo(C₁–C₄)alkoxy, nitro, carboxy, —NR⁶R⁷, —CR⁸=NOR⁹, —NHCOOR¹⁰, —CONR¹¹R¹² or —COOR¹³;

R⁶, R⁷, R⁸, R⁹, R¹⁰, R¹¹, R¹², and R¹³ are a hydrogen atom or (C₁–C₄)alkyl; and

X and Y are each independently a hydrogen atom, halo, cyano, thiocyano or isothiocyano, provided that both X and Y are not a hydrogen atom; or the optical enantiomers thereof.

12. The method of claim 1, 2, 3 or 4 using pyridinecarboxamides having the structural formula

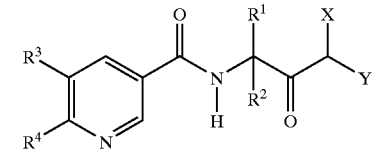

(IV)

wherein

R¹ and R² are each independently a hydrogen atom, (C₁–C₄)alkyl, halo(C₁–C₄)alkyl, (C₂–C₄)alkenyl or (C₂–C₄)alkynyl, provided that both R¹ and R² are not a hydrogen atom;

R³ and R⁴ are each independently a hydrogen atom, halo, cyano, (C₁–C₄)alkyl, halo(C₁–C₄)alkyl, (C₂–C₄) alkenyl, (C₂–C₄)alkynyl, (C₁–C₄)alkoxy, (C₁–C₄) alkylthio, halo(C₁–C₄)alkoxy, nitro, carboxy, —NR⁶R⁷, —CR⁸=NOR⁹, —NHCOOR¹⁰, —CONR¹¹R¹² or —COOR¹³; or R³ and R⁴ taken together may form a fused 5, 6 or 7 membered ring which may contain up to two heteroatoms selected from the group consisting of: O, S, N, and P;

R⁶, R⁷, R⁸, R⁹, R¹⁰, R¹¹, R¹² and R¹³ are each independently a hydrogen atom or (C₁–C₄)alkyl; and X and Y are each independently a hydrogen atom, halo, cyano, thiocyano or isothiocyano, provided that both X and Y are not a hydrogen atom; or the optical enantiomers thereof.

13. The method of claim 12 using pyridinecarboxamides having the structural formula (IV) wherein R¹ is methyl;

R² is methyl or ethyl;

R³ and R⁴ are each independently a hydrogen atom, halo, cyano, methyl, nitro, —NR⁶R⁷, —CR⁸=NOR⁹ or —NHCOOR¹⁰, provided that both R³ and R⁴ are not a hydrogen atom;

R⁶, R⁷, R⁸, R⁹, R¹⁰ and R¹³ are each independently a hydrogen atom or (C₁–C₄)alkyl;

X is chloro and Y is a hydrogen atom; or the optical enantiomers thereof.

14. The method of claim 1, 2, 3 or 4 using furylcarboxamides or thienylcarboxamides having the structural formula

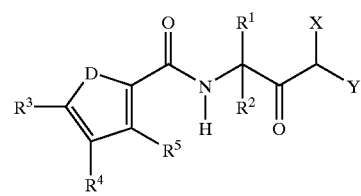

(V)

wherein

D is O or S;

R¹ and R² are each independently a hydrogen atom, (C₁–C₄)alkyl, halo(C₁–C₄)alkyl, (C₂–C₄)alkenyl, and (C₂–C₄)alkynyl, provided that both R¹ and R² are not a hydrogen atom;

R³, R⁴, and R⁵ are each independently a hydrogen atom, halo, cyano, (C₁–C₄)alkyl, halo(C₁–C₄)alkyl, (C₂–C₄) alkenyl, (C₂–C₄)alkynyl, (C₁–C₄)alkoxy, (C₁–C₄) alkylthio, halo(C₁–C₄)alkoxy, nitro, carboxy, —NR⁶R⁷, —CR⁸=NOR⁹, —NHCOOR¹⁰, —CONR¹¹R¹² or —COOR¹³; or R³ and R⁴ taken together may form a fused 5, 6 or 7 membered ring which may contain up to two heteroatoms selected from the group consisting of O, S, N, and P;

R⁶, R⁷, R⁸, R⁹, R¹⁰, R¹¹, R¹², and R¹³ are each independently a hydrogen atom or (C₁–C₄)alkyl; and X and Y are each independently a hydrogen atom, halo, cyano, thiocyano or isothiocyano, provided that both X and Y are not a hydrogen atom; or the optical enantiomers thereof.

15. The method of claim 1, 2, 3 or 4 using furylcarboxamides or thienylcarboxamides having the structural formula

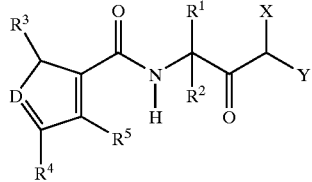

(VI)

wherein

D is O or S;

R$^1$ and R$^2$ are each independently a hydrogen atom, (C$_1$–C$_4$)alkyl, halo(C$_1$–C$_4$)alkyl, (C$_2$–C$_4$)alkenyl, and (C$_2$–C$_4$)alkynyl, provided that both R$^1$ and R$^2$ are not a hydrogen atom;

R$^3$, R$^4$, and R$^5$ are each independently a hydrogen atom, halo, cyano, (C$_1$–C$_4$)alkyl, halo(C$_1$–C$_4$)alkyl, (C$_2$–C$_4$)alkenyl, (C$_2$–C$_4$)alkynyl, (C$_1$–C$_4$)alkoxy, (C$_1$–C$_4$)alkylthio, halo(C$_1$–C$_4$)alkoxy, nitro, carboxy, —NR$^6$R$^7$, —CR$^8$=NOR$^9$, —NHCOOR$^{10}$, —CONR$^{11}$R$^{12}$ or —COOR$^{13}$;

R$^6$, R$^7$, R$^8$, R$^9$, R$^{10}$, R$^{11}$, R$^{12}$ and R$^{13}$ are each independently a hydrogen atom or (C$_1$–C$_4$)alkyl; and X and Y are each independently a hydrogen atom, halo, cyano, thiocyano or isothiocyano, provided that both X and Y are not a hydrogen atom; or the optical enantiomers thereof.

* * * * *

UNITED STATES PATENT AND TRADEMARK OFFICE
CERTIFICATE OF CORRECTION

PATENT NO. : 6,500,405 B1 Page 1 of 1
DATED : December 31, 2002
INVENTOR(S) : David H. Young It is certified that error appears in the above-identified patent and that said Letters Patent is hereby corrected as shown below:

<u>Column 36,</u>
Line 4, should read -- —COOR$^{13}$, or R$^4$ and R$^5$ taken together form a fused 5, -- instead of "—COOR$^3$, or R$^4$ and R$^5$ taken together form a fused 5..."

Signed and Sealed this

Sixteenth Day of March, 2004

JON W. DUDAS
*Acting Director of the United States Patent and Trademark Office*